(12) United States Patent
Dockendorff et al.

(10) Patent No.: US 11,130,743 B2
(45) Date of Patent: Sep. 28, 2021

(54) HETEROCYCLIC LIGANDS OF PAR1 AND METHODS OF USE

(71) Applicant: Marquette University, Milwaukee, WI (US)

(72) Inventors: Christopher Dockendorff, Milwaukee, WI (US); Disha M. Gandhi, Carrboro, NC (US); Ricardo Rosas, Jr., Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 16/827,147

(22) Filed: Mar. 23, 2020

(65) Prior Publication Data

US 2020/0270224 A1 Aug. 27, 2020

Related U.S. Application Data

(63) Continuation of application No. PCT/US2020/019335, filed on Feb. 21, 2020.

(60) Provisional application No. 62/808,680, filed on Feb. 21, 2019.

(51) Int. Cl.
| | | |
|---|---|---|
| *C07D 307/68* | (2006.01) | |
| *C07C 233/80* | (2006.01) | |
| *C07C 233/66* | (2006.01) | |
| *C07D 263/34* | (2006.01) | |
| *C07D 277/587* | (2006.01) | |
| *C07D 233/90* | (2006.01) | |
| *A61P 29/00* | (2006.01) | |

(52) U.S. Cl.
CPC ............ *C07D 307/68* (2013.01); *A61P 29/00* (2018.01); *C07C 233/66* (2013.01); *C07C 233/80* (2013.01); *C07D 233/90* (2013.01); *C07D 263/34* (2013.01); *C07D 277/587* (2013.01)

(58) Field of Classification Search
None
See application file for complete search history.

(56) References Cited

U.S. PATENT DOCUMENTS

| | | | |
|---|---|---|---|
| 6,316,617 | B1 | 11/2001 | Blum |
| 9,422,262 | B2 | 8/2016 | Dockendorff |
| 2013/0331411 | A1 | 12/2013 | Dockendorff |
| 2015/0158867 | A1 | 6/2015 | Schrimpf et al. |

FOREIGN PATENT DOCUMENTS

| | | |
|---|---|---|
| WO | 2012040636 A2 | 3/2012 |
| WO | 2018183122 A1 | 10/2018 |

OTHER PUBLICATIONS

Flaumenhaft et al., Targeting PAR1: Now What? Trends in Pharmacological Sciences, 2017, 38, 701-716.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Adams, M. N. et al. Structure, Function and Pathophysiology of Protease Activated Receptors. Pharmacol. Ther. 2011, 130 (3), 248-282.
Aisuku, O. et al. Parmodulins Inhibit Thrombus Formation Without Inducing Endothelial Injury Caused by Vorapaxar. Blood 2015, 125 (12), 1976-1985.
Barry, G. D. et al. Novel Agonists and Antagonists for Human Protease Activated Receptor 2. J. Med. Chem. 2010, 53 (20), 7428-7440.
Besnard, J.; et al. Automated Design of Ligands to Polypharmacological Profiles. Nature 2012, 492, 215-220.
Bevilacqua, M. P.; et al. Recombinant Tumor Necrosis Factor Induces Procoagulant Activity in Cultured Human Vascular Endothelium: Characterization and Comparison with the Actions of Interleukin 1. Proc. Natl. Acad. Sci. U.S.A. 1986, 83 (12), 4533-4537.
Bouwens, E.; et al. Mechanisms of Anticoagulant and Cytoprotective Actions of the Protein C Pathway. Journal of Thrombosis and Haemostasis 2013, 11 (s1), 242-253.
Brownwell, L. Stop the clots, spare the coagulation. Jan. 15, 2018. Available online at: https://wyss.harvard.edu/news/stop-the-clots-spare-the-coagulation. Version accessed dated Apr. 2, 2019.
Burnier, L. et al. Novel Mechanisms for Activated Protein C Cytoprotective Activities Involving Noncanonical Activation of Protease-Activated Receptor 3. Blood 2013, 122 (5), 807-816.
Carlson, K. E. et al. Pepducins: Lipopeptide Allosteric Modulators of GPCR Signaling. Drug Discovery Today: Technologies 2012, 9 (1), e33-e39.
Chen, J. et al. Thrombin Receptor Activation. Confirmation of the Intramolecular Tethered Liganding Hypothesis and Discovery of an Alternative Intermolecular Liganding Mode. J. Biol. Chem. 1994, 269 (23), 16041-16045.
Chu, A. J. Tissue Factor Mediates Inflammation. Arch. Biochem. Biophys. 2005, 440 (2), 123-132.
Colucci, M. et al. Cultured Human Endothelial Cells Generate Tissue Factor in Response to Endotoxin. Journal of Clinical Investigation 1983, 71 (6), 1893-1896.
Covic, L. et al. Activation and Inhibition of G Protein-Coupled Receptors by Cell-Penetrating Membrane-Tethered Peptides. Proc. Natl. Acad. Sci. U.S.A. 2002, 99 (2), 643-648.

(Continued)

*Primary Examiner* — Po-Chih Chen
(74) *Attorney, Agent, or Firm* — Quarles & Brady LLP

(57) ABSTRACT

The present invention provides novel compounds with increased plasma stability that modulate PAR1 signaling, and methods of using them. The present invention provides methods of using the novel PAR1 modulators for the treatment of a number of disorders, including, inflammation, thrombosis, kidney disease, sepsis, stroke, as well as proliferation-related diseases. Furthermore, the PAR1 modulators of the present invention provide cytoprotection for certain cells and tissues, for example, in coronary blood vessels and tissues after a heart attack.

16 Claims, 7 Drawing Sheets

(56) References Cited

OTHER PUBLICATIONS

Cunningham, M. et al. Proteinase-Activated Receptors (PARs) as Targets for Antiplatelet Therapy. Biochemical Society Transactions 2016, 44 (2), 606-612.

De Ceunynck, K., et al. "PAR1 agonists stimulate APC-like endothelial cytoprotection and confer resistance to thromboinflammatory injury." Proceedings of the National Academy of Sciences 115.5 (2018): E982-E991.

Dockendorff, C., et al. Discovery of 1,3-Diaminobenzenes as Selective Inhibitors of Platelet Activation at the PAR1 Receptor. ACS Med Chem Lett 2012, 3 (3), 232-237.

Dowal, L. et al. Identification of an Antithrombotic Allosteric Modulator That Acts Through Helix 8 of PAR1. Proceedings of the National Academy of Sciences 2011, 108 (7), 2951-2956.

Gandhi, D. M., et al. "Characterization of Protease-Activated Receptor (PAR) ligands: Parmodulins are reversible allosteric inhibitors of PAR1-driven calcium mobilization in endothelial cells." Bioorganic & medicinal chemistry 26.9 (2018): 2514-2529.

Gandhi, D. M.; et al. The parmodulin NRD-21 is an allosteric inhibitor of PAR1 Gq signaling with improved anti-inflammatory activity and stability. Bioorganic & Medicinal Chemistry 2019, 27 (7), 3788-3796.

Gando, S. et al. Disseminated Intravascular Coagulation. Nat Rev Dis Primers 2016, 2, 16037.

Hamilton, J. R. et al. Challenges and Opportunities in Protease-Activated Receptor Drug Development. Annu. Rev. Pharmacol. Toxicol. 2017, 57 (1), 349-373.

Hollenberg, M. D. et al. Biased Signalling and Proteinase-Activated Receptors (PARs): Targeting Inflammatory Disease. British Journal of Pharmacology 2014, 171 (5), 1180-1194.

International Searching Authority, International Search Report & Written Opinion for application PCT/US2020/019335. dated May 14, 2020.

Kawabata, A., et al. "Evaluation of proteinase-activated receptor-1 (PAR1) agonists and antagonists using a cultured cell receptor desensitization assay: activation of PAR2 by PAR1-targeted ligands." Journal of Pharmacology and Experimental Therapeutics 288.1 (1999): 358-370.

Madhusudhan, T. et al. Cytoprotective Signaling by Activated Protein C Requires Protease-Activated Receptor-3 in Podocytes. Blood 2012, 119 (3), 874-883.

Mosnier, L. O. et al. Biased Agonism of Protease-Activated Receptor 1 by Activated Protein C Caused by Noncanonical Cleavage at Arg46. Blood 2012, 120 (26), 5237-5246.

Mosnier, L. O. et al. Inhibition of Staurosporine-Induced Apoptosis of Endothelial Cells by Activated Protein C Requires Protease-Activated Receptor-1 and Endothelial Cell Protein C Receptor. Biochem. J. 2003, 373 (Pt 1), 65-70.

Nawroth, P. P. et al. Modulation of Endothelial Cell Hemostatic Properties by Tumor Necrosis Factor. J. Exp. Med. 1986, 163 (3), 740-745.

Nazir, S. et al. Cytoprotective Activated Protein C Averts Nlrp3 Inflammasome-Induced Ischemia-Reperfusion Injury via mTORC1 Inhibition. Blood 2017, 130 (24), 2664-2677.

Ramachandran, R. et al. Agonist-Biased Signaling via Proteinase Activated Receptor-2: Differential Activation of Calcium and Mitogen-Activated Protein Kinase Pathways. Molecular Pharmacology 2009, 76 (4), 791-801.

Ramachandran, R. et al. Targeting Proteinase-Activated Receptors: Therapeutic Potential and Challenges. Nat Rev Drug Discov 2012, 11 (1), 69-86.

Rasmussen, U. B. et al. A Peptide Ligand of the Human Thrombin Receptor Antagonizes Alpha-Thrombin and Partially Activates Platelets. J. Biol. Chem. 1993, 268 (19), 14322-14328.

Schuepbach, R. A. et al. Protease-Activated Receptor-1 Cleaved at R46 Mediates Cytoprotective Effects. J. Thromb. Haemost. 2012, 10 (8), 1675-1684.

Sevigny, L. M. et al. Interdicting Protease-Activated Receptor-2-Driven Inflammation with Cell-Penetrating Pepducins. Proceedings of the National Academy of Sciences 2011, 108 (20), 8491-8496.

Soh, U. J. et al. Activated Protein C Promotes Protease-Activated Receptor-1 Cytoprotective Signaling Through ?—Arrestin and Dishevelled-2 Scaffolds. Proc. Natl. Mad. Sci. U.S.A. 2011, 108 (50), E1372-E1380.

Suen, J. Y. et al. Modulating Human Proteinase Activated Receptor 2 with a Novel Antagonist (GB88) and Agonist (GB110). British Journal of Pharmacology 2012, 165 (5), 1413-1423.

Verplank, L. et al. Chemical Genetic Analysis of Platelet Granule Secretion-Probe 3; National Center for Biotechnology Information (US): Bethesda (MD), 2010.

Zhang, P. et al. Allosteric Activation of a G Protein-Coupled Receptor with Cell-Penetrating Receptor Mimetics. Journal of Biological Chemistry 2015, 290 (25), 15785-15798.

* cited by examiner

Table 5. Comparison of ML161 and NRD-21

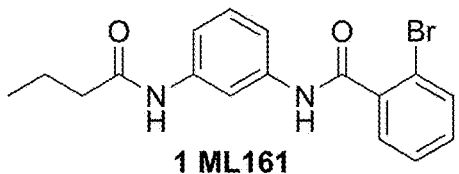 

1 ML161      38 NRD-21

| | ML161 | NRD-21 |
|---|---|---|
| $IC_{50} \pm SEM^a$ | 0.57 ± 0.08 (n = 10) | 0.37 ± 0.13 (n = 6) |
| Plasma stability | <1% (4 h, mouse) | 32% (4 h, mouse) |
| Microsomal stability | >99% (1 h, human) | >99% (1 h, human) |
| Kinetic aqueous solubility (2.5% DMSO) | 24 μM | 17 μM |
| PAR2 activity? | None observed | None observed |
| Cytotoxicity ($CC_{50}$) (human hepG2 cells) | >150 μM | >150 μM |
| Reversible? | Yes | Yes |

[a]Average of independent assays, each with $IC_{50}$s determined from curve fits with n = 3.

FIG. 7

HETEROCYCLIC LIGANDS OF PAR1 AND METHODS OF USE

CROSS-REFERENCE TO RELATED APPLICATIONS

This application is a continuation application of PCT Application No. PCT/US2020/019335 filed on Feb. 21, 2020, which claims priority to U.S. Provisional Application No. 62/808,680 filed on Feb. 21, 2019, the contents of which are incorporated by reference in their entireties.

STATEMENT REGARDING FEDERALLY SPONSORED RESEARCH

This invention was made with government support under R15 HL127636 awarded by the National Institutes of Health. The government has certain rights in the invention.

BACKGROUND OF THE INVENTION

The field of the invention is related to novel heterocyclic ligands of PAR1 and methods of use.

Protease-activated receptors (PARs) are a unique family of class A G-protein-coupled receptors (GPCRs) that are activated by extracellular proteases such as thrombin and trypsin and mediate a range of important signaling pathways in numerous tissues.[1,2] PARs are present in a variety of tissues and are implicated in a variety of pathologies including thrombosis, inflammation, and cancer cell metastasis.[3,4] The use of biased ligands for G-protein coupled receptors (GPCRs) has emerged as a promising strategy for maximizing therapeutic signals mediated by GPCRs, while potentially mitigating undesired side effects linked to alternative signaling pathways initiated by the same receptors. The varied phenotypic effects of PAR activation have recently been connected to the activation of specific G-proteins and arrestins,[5] and biased signals have been observed with proteases such as activated protein C (aPC) that cleave PAR N-termini at alternative sites.[6-10] Synthetic peptides[11,12] and peptidomimetics[13,14] based on PAR tethered ligands have also shown biased signaling by blocking or activating only a subset of signals, and pepducins, a novel class of fatty acid-tethered peptides modeled after intracellular GPCR loops developed by Kuliopulos and coworkers,[15-17] have been reported to act as biased antagonists at PAR2.[4,18] Previously, the inventors reported that small molecules identified via high-throughput screening (HTS) are capable of inhibiting platelet granule secretion, while permitting the shape change of platelets normally observed upon platelet activation via PAR1 agonism, thus acting as "biased antagonists" of PAR1.[19,20] These small molecules, termed parmodulins, act at the intracellular side of PAR1 to block signaling mediated by Gq, but not G12/13.[21,22] The parmodulin ML161 (1, also referred to as parmodulin 2 or PM2, FIG. 1A) was found to promote cytoprotective and anti-inflammatory effects in endothelium in a manner similar to aPC,[22] and as with aPC it was highly effective at minimizing necrosis of coronary tissue in a mouse model of myocardial infarction (MI).[23] ML161 and its aniline analog RR-90 are selective, reversible, and allosteric inhibitors (negative allosteric modulators) of PAR1 signaling via the G-protein Gq.[24]

However, ML161 has been found to have low stability in plasma.[20] There is a need to identify related ligands that modulate PAR1 but maintain their stability in plasma and other biological medium in order to provide optimum potency in an in vivo environment.

SUMMARY OF THE INVENTION

The present invention overcomes the aforementioned drawbacks by providing compounds which are modulators of PAR1 with improved plasma stability. These compounds can be used for the prevention of thrombosis and treatment of cardiovascular diseases, as well as inflammation-related conditions such as sepsis, ischemia-reperfusion conditions, stroke, and kidney disease, as well as proliferative disorders such as fibrosis and cancer.

In one aspect, the present disclosure provides a compound of formula I:

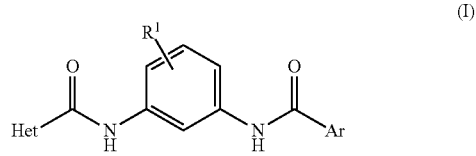

wherein Het is selected from the group consisting of

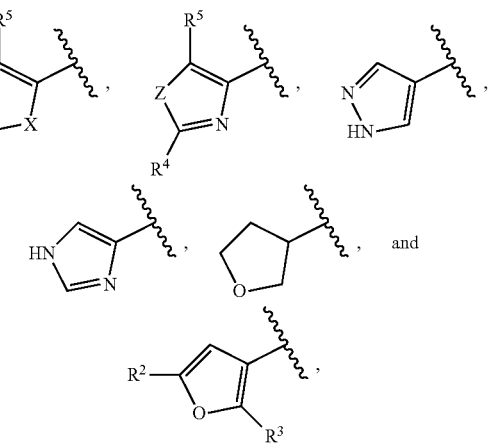

where $R^1$ is H, Me, F, or Cl, $R^2$ and $R^3$ are each independently selected from a H or a halogen, $R^4$ and $R^5$ are each independently selected from H, Me, F, Cl, Br or fluoroalkyl, X and Z are independently selected from O, S, and NH, and Ar is a substituted benzene with at least one substitution selected from the group consisting of Br, Cl, F, —OH, fluoroalkyl and fluoroalkoxy.

In another aspect, the compound is a compound of formula I wherein Het is selected from the group consisting of:

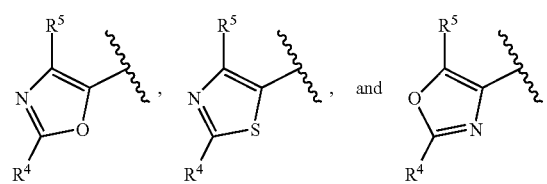

wherein $R^4$ and $R^5$ are each independently selected from H, Me, F, Cl, and Br.

In yet another aspect, the compound is a compound of formula I wherein Het is

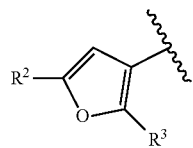

wherein R² is H and R³ is a halogen; R³ is H and R² is a halogen; or both R² and R³ are H.

In another aspect, the compound is of formula I, wherein Het is selected from the group consisting of:

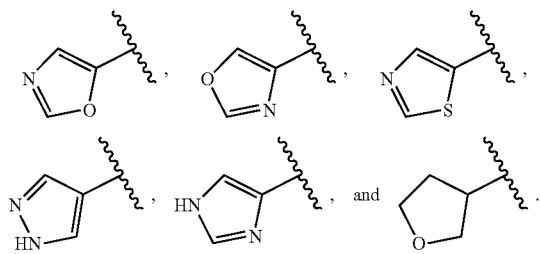

In another aspect, the compound is selected from the group consisting of:

NRD-21

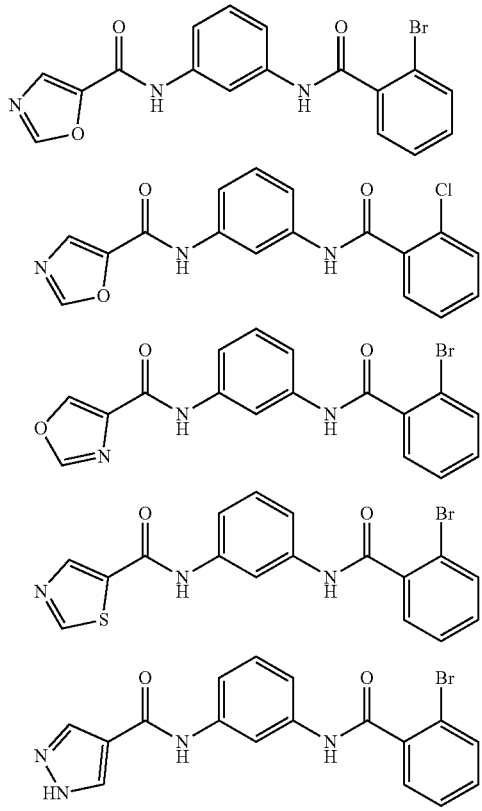

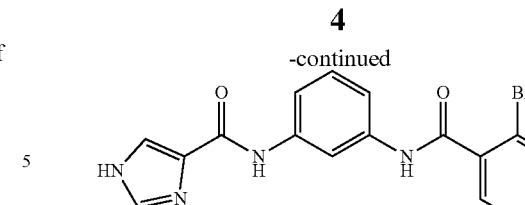

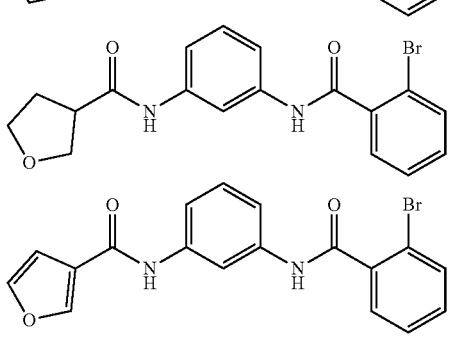

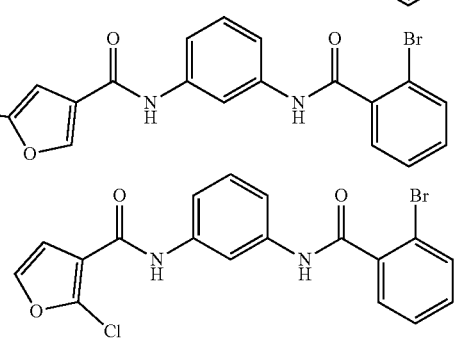 and

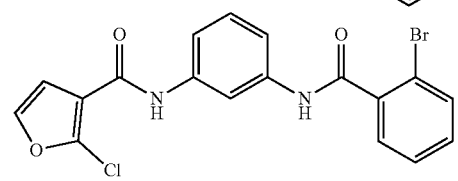

These compounds showed good potency, as tested by a PAR1-mediated intracellular calcium mobilization assay with endothelial cells.

In one aspect, the disclosure provides a compound:

NRD-21

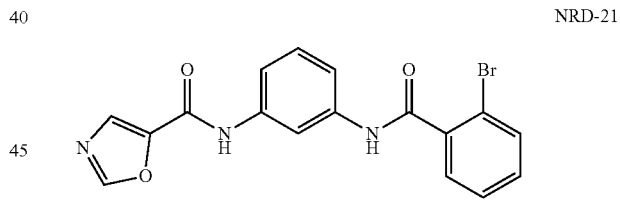

In another aspect, the disclosure provides a composition comprising the compound of formula I described herein and a pharmaceutically acceptable carrier.

In yet another aspect, the disclosure provides a method of reducing, inhibiting or preventing thrombosis in a subject having or suspected of having a cardiovascular disease, the method comprising administering an effective amount of the compound of formula I described herein or the composition comprising the compound of formula I described herein to reduce, inhibit or prevent thrombosis.

In another aspect, the disclosure provides a method of treating an inflammatory condition in a subject, the method comprising administering an effective amount of the compound of formula I described herein or the composition comprising the compound of formula I described herein to treat the inflammatory condition.

In another aspect, the disclosure provides a method of treating sepsis in a subject having sepsis, the method comprising administering an effective amount of the compound of formula I described herein or the composition comprising the compound of formula I described herein to treat the sepsis.

In yet a further embodiment, the disclosure provides a method of treating kidney disease in a subject having kidney disease, the method comprising administering an effective amount of the compound of formula I described herein or the composition comprising the compound of formula I described herein to treat the kidney disease.

In yet another aspect, the disclosure provides a method of treating fibrosis in a subject having fibrosis, the method comprising administering an effective amount the compound of formula I described herein or the composition comprising the compound of formula I described herein to treat the fibrosis.

In yet another aspect, the disclosure provides a method of treating a proliferative disorder in a subject, the method comprising administering an effective amount of the compound of formula I described herein or the composition comprising the compound of formula I described herein to treat the proliferative disorder.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and description herein for interpreting the scope of the invention.

BRIEF DESCRIPTION OF THE DRAWINGS

FIG. 7 provides Table 5 showing a comparison of ML161 and NRD-21.

DETAILED DESCRIPTION OF THE INVENTION

Figures 1A, 1B, 1C, 1D:
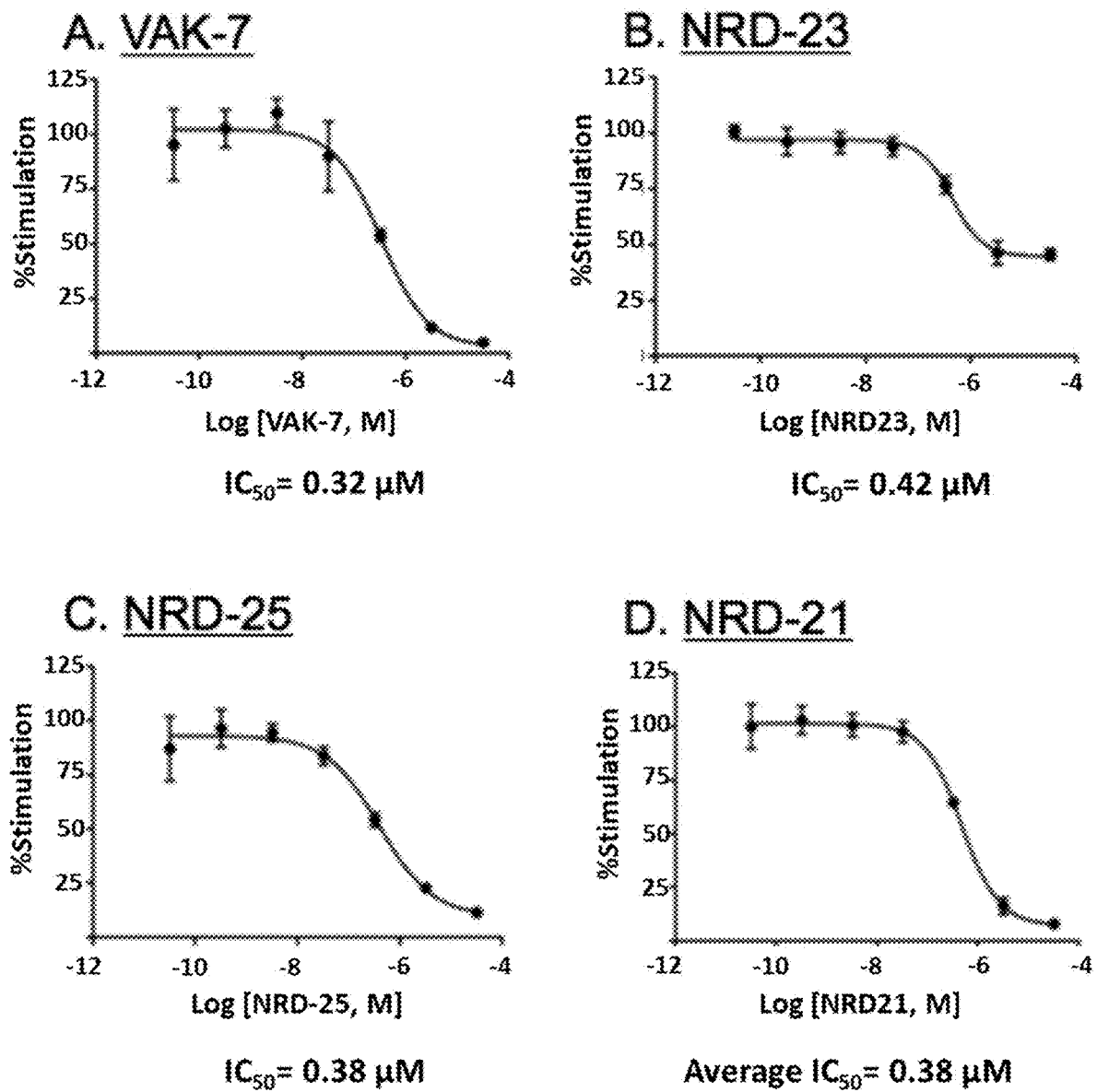
FIGS. 1A-1D depicts concentration-response curves for PAR1 antagonists in the TFLLRN-NH$_2$-mediated (5 µM) intracellular calcium mobilization (iCa$^{2+}$) assay with Ea.hy926 cells: A) 35 (VAK-7), B) 39 (NRD-23), C) 9 (NRD-25), D) 38 (NRD-21). Cells were loaded with the calcium-binding dye Fluo-4/AM, and changes in calcium concentration were measured with a plate reader.
Figures 2A, 2B:
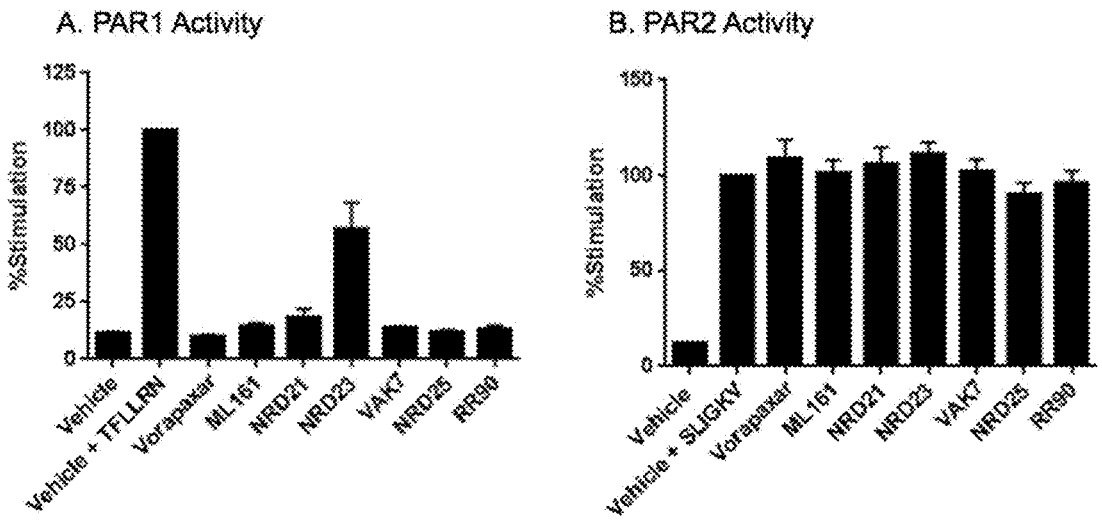
FIGS. 2A-2B depicts selectivity data of antagonists in A) PAR1 (TFLLRN-NH$_2$)-and B) PAR2 (SLIGKV-NH$_2$)-driven intracellular calcium mobilization (iCa$^{2+}$) with Ea.hy936 cells. Parmodulins were used at 10 µM; vorapaxar was used at 0.316 µM. PAR1 agonist TFLLRN-NH$_2$ and PAR2 agonist SLIGKV-NH$_2$ were used at 3.16 µM; Vehicle (V)=10% DMSO/water.
Figure 3:
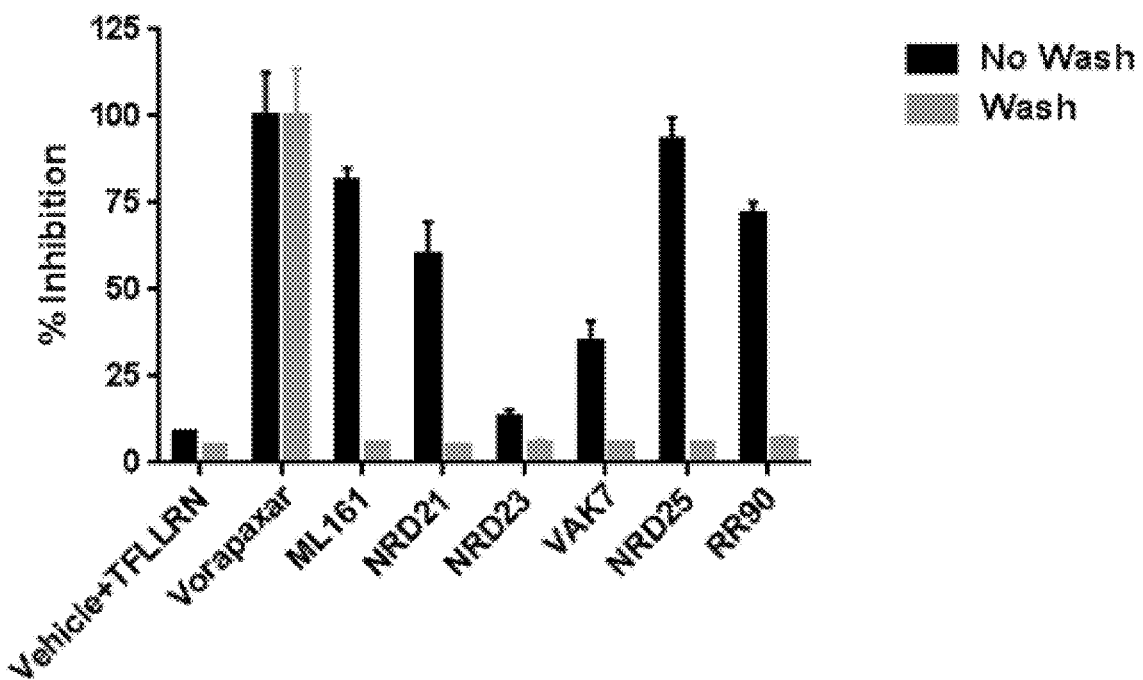
FIG. 3 depicts reversibility studies of the PAR1 antagonist vorapaxar and selected parmodulins in the intracellular calcium mobilization (iCa$^2$+) assay. Parmodulins were used at 10 µM; vorapaxar was used at 0.316 µM. PAR1 agonist TFLLRN-NH$_2$ and PAR2 agonist SLIGKV-NH$_2$ were used at 3.16 µM; Vehicle (V)=10% DMSO/water. Cells containing antagonist were washed with buffer prior to the treatment with PAR1 agonist TFLLRN-NH$_2$ (5 µM).
Figure 4:
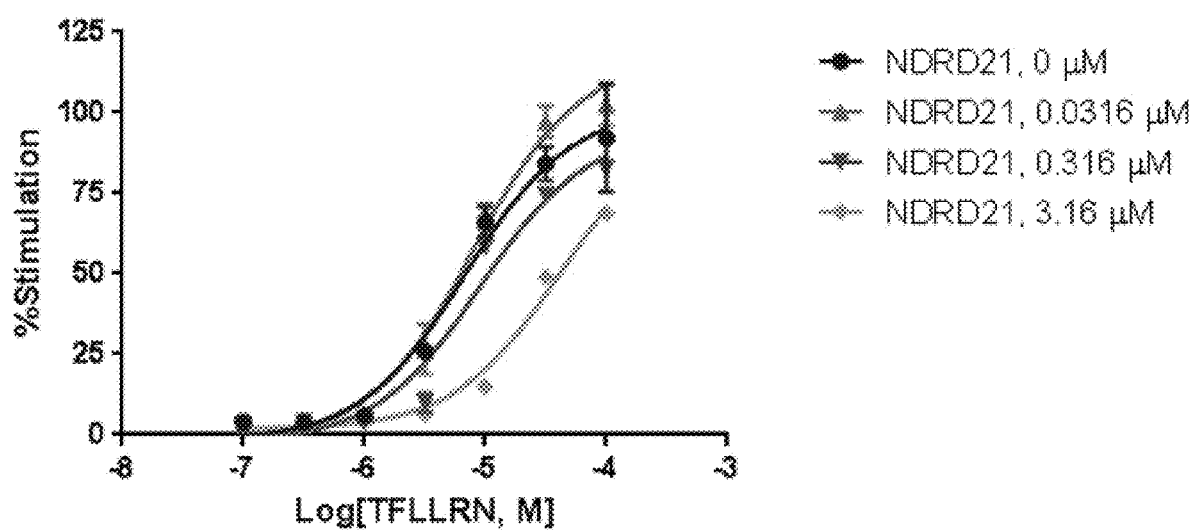
FIG. 4 depicts iCa$^{2+}$ concentration-response of the PAR1 agonist TFLLRN-NH$_2$ in the presence of increasing concentrations of NRD-21.

The present disclosure is directed to compounds that are able to modulate PAR1 activation with increased plasma stability. Unlike prior compounds, such as ML161, which have low plasma stability, the present compounds exhibit inhibition of PAR1-driven calcium mobilization along with increased plasma stability, providing unexpectedly better properties than the prior compounds.

In one embodiment, the disclosure provides a compound of formula I:

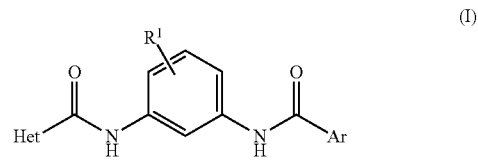

wherein Het is selected from the group consisting of

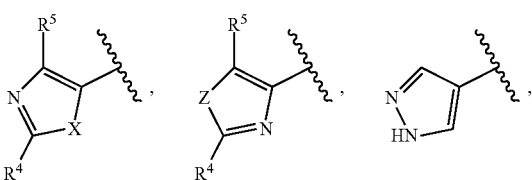

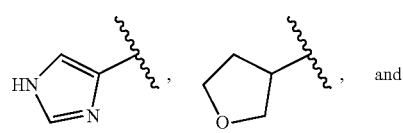

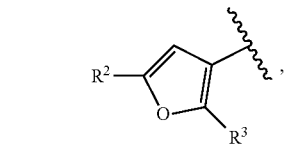

Where $R^1$ is H, Me, F, or Cl; $R^2$ and $R^3$ are each independently selected from a H or a halogen; $R^4$ and $R^5$ are each independently selected from H, Me, F, Cl, Br or haloalkyl, X is either O or S; Z is either O or NH, and Ar is a substituted benzene with at least one substitution selected from the group consisting of Br, F, Cl, —OH, haloalkyl and haloalkoxy In one embodiment, the compound of formula I comprises a Het selected from the group consisting of:

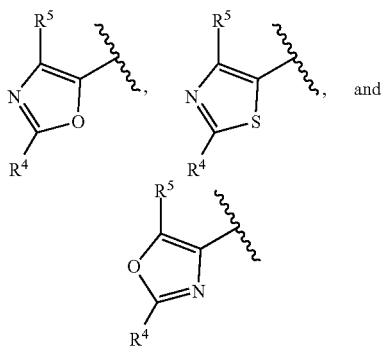

wherein $R^4$ and $R^5$ are each independently selected from H, Me, F, Cl, and Br. In one example, both $R^4$ and $R^5$ are H. In another example, either $R^4$ or $R^5$ is F, Cl or Br, and the other is H. In one example, $R^5$ is H, and $R^4$ is Br. In another example, $R^5$ is H, and $R^4$ is Cl. In another example, $R^5$ is H, and $R^4$ is F. In another example, $R^4$ is H, and $R^5$ is Br. In a further example, $R^4$ is H, and $R^5$ is Cl. In another example, $R^4$ is H, and $R^5$ is F.

In another embodiment of formula (I), Het is

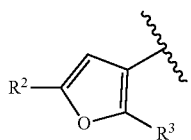

wherein $R^2$ is H and $R^3$ is a halogen (e.g., Br, Cl, F); $R^3$ is H and $R^2$ is a halogen (e.g., Br, Cl, F); or both $R^2$ and $R^3$ are H. In one example, both $R^2$ and $R^3$ are H. In another example, $R^2$ is Br and $R^3$ are H. In another example, $R^2$ is H and $R^3$ are Cl.

In another embodiment formula (I) comprises a Het is selected from the group consisting of:

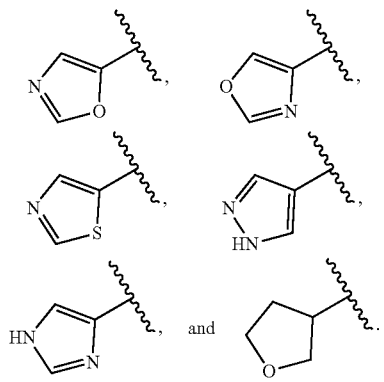

In some embodiments of formula (I), Ar is a benzene substituted with one halogen selected from Br, Cl, and F. For example, in some embodiments, the Ar is 2-bromobenzene. In other examples, Ar is a 2-chlorobenzene. In further embodiments, Ar is a benzene substituted with Br and at least one additional substitution selected from the group consisting of F, Cl and OH.

In some embodiments, the present disclosure provides a compound of one of the following:

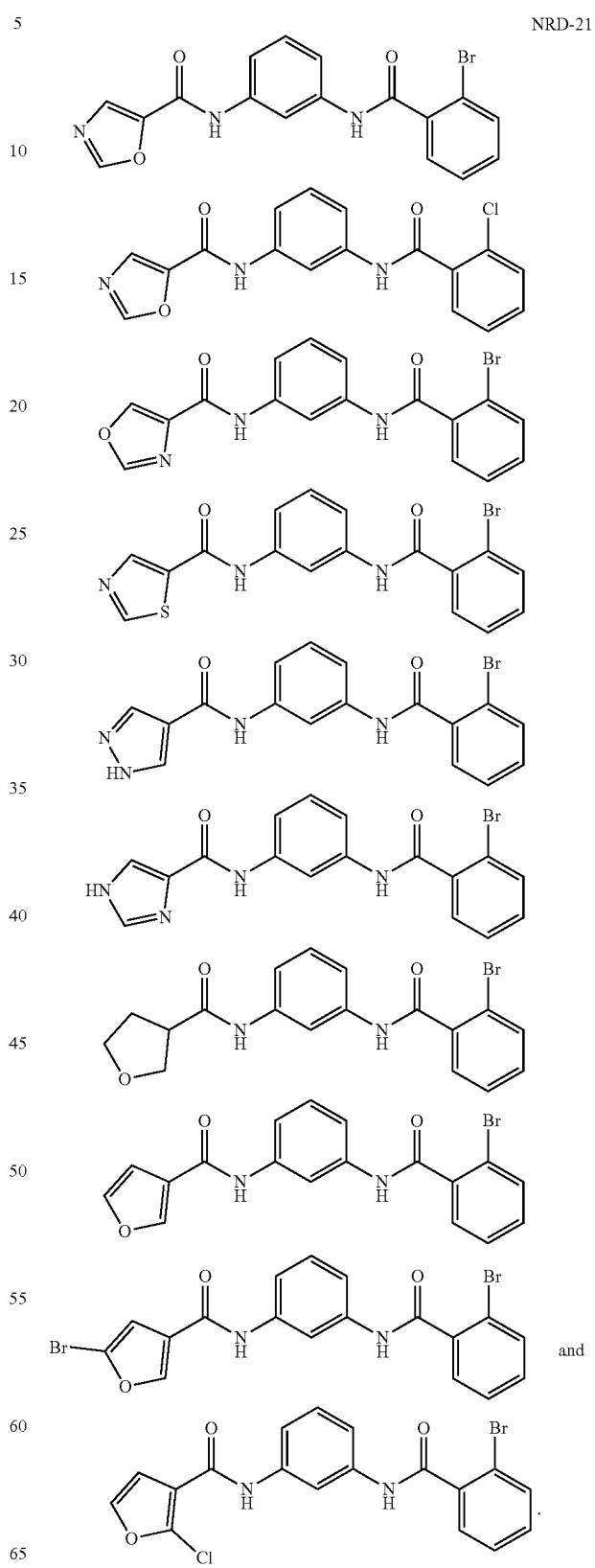

and

The present disclosure further provides a compound of formula I:

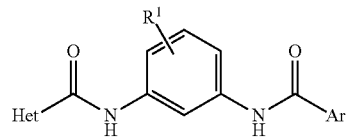
(I)

wherein Het is selected from the group consisting of

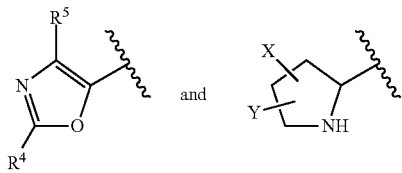
and wherein $R^1$ is H, Me, CN, F, Cl, Br, or

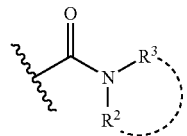

$R^2$ and $R^3$ are each independently selected from H or alkyl, or $R^2$ and $R^3$ together are a C3-05 alkyl to form a 4-6 member ring,
$R^4$ and $R^5$ are independently selected from H, Me, F, Cl or Br,
X and Y are independently selected from H, F, alkyl, —OH, alkoxy, halogen substituted alkoxy, wherein if X and Y are on the same carbon, X and Y is alkenyl (=$CR_2$) or carbonyl (=O) and R is H or an alkyl; and
Ar is a substituted benzene.

In some particular embodiments, the compound of formula I comprises Het selected from the group consisting of:

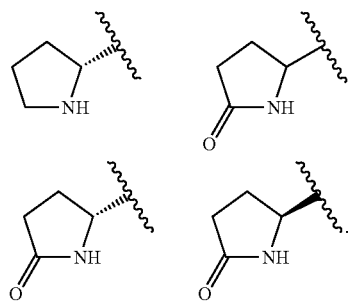

In another embodiment, the compound I comprises Het selected from the group consisting of:

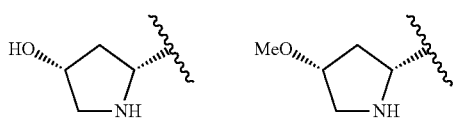

-continued

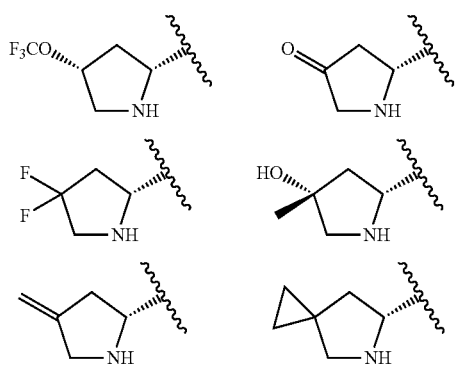

In some embodiments, the Ar in the compound of formula I is a substituted benzene with at least one substitution selected from the group consisting of Br, F, Cl, —OH fluoroalkyl and fluoroalkoxy. In a particular embodiment, Ar is 2-bromobenzene. In another example, Ar is a benzene substituted with Br and at least one additional substituent selected from the group consisting of F, Cl and OH. In another embodiment, the Ar is 2-chlorobenzene. In another embodiment, Ar is $CF_3$ or $OCF_3$. Other suitable substituted benzenes are contemplated within the structure of the invention.

In one embodiment, the compound is:

NRD-21

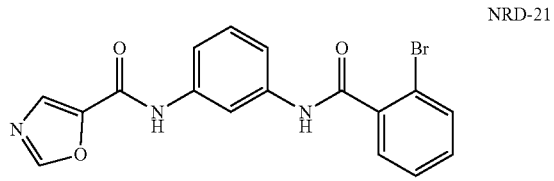 [SMILES: O=C(Nc1cccc(NC(=O)c2ccccc2Br)c1)c1cnco1]

In another embodiment, the compound is a compound of formula I:

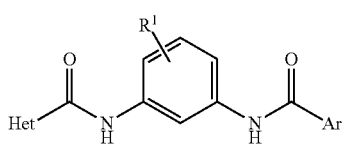
(I)

wherein Ar is a substituted benzene, and Het is selected from the group consisting of:

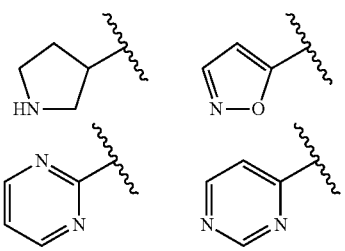

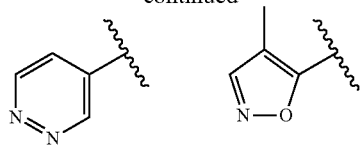

As used herein, the term "alkyl" includes alkoxy, alkylamino, alkoxycarbonyl and alkylaminocarbonyl, a straight-chain or branched alkyl radical having 1 to 6 carbon atoms. For example, suitable alkyls include, but are not limited to, methyl, ethyl, n-propyl, isopropyl, n-butyl, tert-butyl, n-pentyl and n-hexyl.

The term "alkoxy" refers to an alkyl (carbon and hydrogen chain) group singularly bonded to an oxygen, i.e. R-O. The alkoxy can contain a halogen-substituted alkyl, for example, an alkyl substituted with fluorine, chlorine, bromine, or iodine. In some embodiments, the haloalkoxy can be substituted with one or more halogens, for example, 2 or 3 halogens (e.g., but not limited to O—$CF_3$).

The term "haloalkyl" refers to an alkyl chain (carbon and hydrogen chain) having one or more of the hydrogens substituted with a halogen, e.g., Br, F, Cl, or I. The term "fluoroalkyl" is an alkyl chain having one or more hydrogens substituted with fluorine (F), e.g., a suitable haloalkyl is —$CF_3$. However, the disclosure is not limited to these examples, and one skilled in the art would be able to determine suitable haloalkyl substitutions.

Halogen or halo refers to with fluorine, chlorine, bromine, or iodine.

In another embodiment, the present disclosure provides a composition comprising or consisting essentially of the compound of formula I described above and a pharmaceutically acceptable carrier.

A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically phosphate buffer saline or other saline solutions are physiologically acceptable carriers. In some embodiments, additional components may be add to preserve the structure and function of the compounds of the present invention, but are physiologically acceptable for administration to a subject. The carrier(s) must be acceptable in the sense of being compatible with the other ingredients of the formulation and not deleterious to the recipient thereof.

Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The composition according to the present invention may be formulated for oral administration, parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form for constitution with a suitable vehicle, e.g. sterile, pyrogen-free water, before use.

The compounds described herein are effective regulators of PAR1 signaling and platelet activation, and can be used as anti-inflammatories and anti-thrombotic agents, among other uses. Methods of PAR1 activity may be assessed by various methods known in the art. For example, a useful compound can be identified by its ability to inhibit PAR1-driven signals such as TFLLRN-$NH_2$ or thrombin-induced intracellular calcium flux (e.g., $iCa^{2+}$ mobilization assay), platelet aggregation, or P-selectin expression. Additional assays are described by Kawabata, et al., J Pharmacol Exp Ther. (1999) 288(1):358-70. Alternatively, a PAR1 activator can be identified for its ability to promote PAR1-driven protective signaling, such as the decrease in tissue factor expression or Factor X activation in response to toxins such as TNF-alpha.[22]

Inhibition occurs when PAR1 intracellular signaling driven by a suitable agonist or activator (such as thrombin) is inhibited, as measured for example by intracellular calcium mobilization in PAR1-expressing cells or organisms exposed to a compound of the invention. This inhibition can be at least about 10% less, for example, at least about 25%, 50%, 75% less, 80% less, 90% less, or totally inhibited, in comparison to intracellular signaling from control cells or organisms not exposed to the compound.

The terms "compound" as used herein include all pharmaceutically acceptable salts, co-crystals, solvates, hydrates, polymorphs, enantiomers.

The term "plasma stability" as used herein refers to the ability of the compound to remain intact after incubation with plasma, for example, mouse plasma or human plasma, after a certain period of time. For example, the compounds of the present invention (e.g., compounds of formula I) have a greater half-life for plasma stability than prior compounds (for example, greater half-life stability than ML161). Methods of determining the plasma stability of the compounds are known in the art. For example, one can measure the amount of compound remaining by HPLC after a 4 h incubation in plasma, or if multiple time points are taken, a half-life for plasma stability can be calculated. As described in the Examples and Table 5, the % compound remaining after 4 h-incubation in mouse plasma is substantially better than the compounds of the prior art (e.g., ML161). For example, increased plasma stability can be at least 20% of the compound remains after 4 hour incubation in plasma, alternatively at least 30% of the compound remains after 4 hour incubation in plasma.

Methods of Treatment

Methods of the present disclosure include methods of using the compounds and pharmaceutical compositions described herein for the treatment of a subject in need thereof. In some embodiments, the compounds are used to treat any disease associated with PAR1 signaling.

In one embodiment, the present disclosure provides methods of treating thrombosis in a subject having or suspected of having thrombosis. The method comprises administering an effective amount of a compound described herein or a composition including the compound to reduce, inhibit or prevent thrombosis.

The invention provides methods for reducing platelet activation, reducing platelet aggregation, and reducing thrombosis. The invention further provides methods of treating or preventing diseases or disorders in which the pathology of the disease or disorder involves one or more of platelet activation, platelet aggregation and thrombus formation.

The invention encompasses a method of reducing platelet activation, platelet aggregation or thrombosis, the method comprising administering an effective amount of a compound of Formula I or a pharmaceutically acceptable salt thereof, such that platelet activation, aggregation or thrombosis is reduced. Thrombosis is the formation of a blood clot inside a blood vessel resulting in obstructing the flow of blood through the circulatory system. Thrombosis may be the result, for example, of blood vessel injury (i.e. a vein or an artery is injured), an unnatural or lack of circulation of blood, or rupture of plaque from an artery, and may result in myocardial infarction, ischemic disease, or stroke. Once blood vessels are injured, the body uses platelets and fibrin to form a blood clot to prevent blood loss. In some embodiments, the disease or disorder that results from thrombosis is selected from the group consisting of: acute myocardial infarction; stable angina; unstable angina; transient ischemic attack; coronary artery disease, cerebrovascular disease; peripheral vascular disease; placental insufficiency; thrombosis subsequent to or associated with a surgical procedure; thrombosis associated with atrial fibrillation; and inflammation.

In a preferred embodiment, the inflammation is inflammation associated with wound healing, atherosclerosis or allergy. In another embodiment, the surgical procedure is selected from the group consisting of: aortocoronary bypass surgery; coronary angioplasty; stent placement; and insertion of prosthetic heart valves.

In another embodiment, the present disclosure provides a method of treating ischemic disease or stroke. The method comprises administering an effective amount of a compound of Formula I or a pharmaceutically acceptable salt thereof, such that the ischemic disease or stroke is treated.

The invention further relates to a method of treating a vascular disorder associated with increased PAR1 levels by administering a compound of Formula I to a subject in need thereof. The increased level of PAR1 can be determined by any number of methods readily available to one skilled in the art.

In another embodiment, the disclosure provides a method of treating an inflammatory condition in a subject, the method comprising administering an effective amount of the compound of formula I described herein or the composition comprising the compound of formula I described herein to treat the inflammatory condition. Suitably, the compounds described herein can treat inflammation-related conditions such as sepsis, ischemia-reperfusion conditions, stroke, and kidney disease. Prior reports of the parmodulin (i.e., PAR1 modulators) showed their ability to act as anti-inflammatories. The current compounds provide plasma stable compounds that can provide anti-inflammatory activity. See, e.g., Gandhi, D. M.; et al. The parmodulin NRD-21 is an allosteric inhibitor of PAR1 Gq signaling with improved anti-inflammatory activity and stability. *Bioorganic & Medicinal Chemistry* 2019, 27 (7), 3788-3796, incorporated by reference in its entirety.

The present disclosure also provides methods of treating sepsis in a subject. The method comprises administering an effective amount of a compound of Formula I or a pharmaceutically acceptable salt thereof, such that sepsis is treated. Sepsis (or septicaemia) is a frequent disorder with high mortality. Initial symptoms of sepsis are typically unspecific (for example fever, reduced general state of health); however, as the disorder progresses there may be a general activation of the coagulation system ("disseminated intravascular coagulation" or "consumption coagulopathy" (DIC)) with the formation of microthrombi in various organs and secondary bleeding complications. DIC may also occur independently of a sepsis, for example during surgical interventions or associated with tumor disorders. The present compounds and compositions are contemplated for use in treating sepsis and DIC.

In another embodiment, the present disclosure provides methods of treating kidney disease in a subject comprising administering an effective amount of a compound of Formula I or a pharmaceutically acceptable salt thereof, such that the kidney disease is treated.

The present disclosure further contemplates treating fibrosis, and other proliferative disorders. Fibrosis is the formation of excess fibrous connective tissue in an organ or tissue in a reparative or reactive process in response to injury (scarring) or arising from single cells (fibroma). Physiologically, fibrosis interferes with or totally inhibits the normal architecture and function of the underlying organ or tissue. The method of treating fibrosis comprises administering an effective amount of a compound of Formula I or a pharmaceutically acceptable salt thereof, to treat the fibrosis.

The present disclosure further contemplates treating a proliferative disorder in a subject, in particular proliferative diseases of endothelial cells, fibroblasts, nephrocytes, osteosarcoma cells, muscle cells, cancer cells and/or glia cells, or malignancies such as cancer of the breast, lung, brain, kidney, skin, prostate, ovary or colon, among others. The method comprises administering to a subject suffering from the disease a therapeutically effective dose of a compound of Formula I or composition comprising the compound of formula I. In a particular embodiment, the proliferative disorder is cancer or restenosis.

The present invention provides a method of treating a subject having cancer, the method comprising administering the compound or the composition comprising the compound to the subject in an effective amount to treat the cancer.

In another embodiment, the present disclosure provides a method of inhibiting, reducing, or preventing metastasis in a patient having cancer, the method comprising administering the compound or the composition comprising the compound to the subject in an effective amount to reduce or inhibit metastasis of the cancer in the subject.

The terms "metastasis" or "secondary tumor" refer to cancer cells that have spread to a secondary site, e.g., outside of the original primary cancer site. Secondary sites include, but are not limited to, for example, the lymphatic system, skin, distant organs (e.g., liver, stomach, pancreas, brain, etc.), and the like, and will differ depending on the site of the primary tumor.

For purposes of the present invention, "treating" or "treatment" describes the management and care of a subject for the purpose of combating the disease, condition, or disorder. Treating includes the administration of a compound of present invention to prevent the onset of the symptoms or complications, alleviating the symptoms or complications, or eliminating the disease, condition, or disorder. Treating also encompasses therapeutic and palliative treatment. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. A therapeutically effective amount of the compound or compositions described herein may vary according to factors such as the disease state, age, sex, and weight of the subject, and the ability of the disclosed compounds to elicit a desired response in the subject. Dosage regimens may be adjusted to provide the optimum therapeutic response. A therapeutically effective amount is also one in which any toxic or detrimental effects of the disclosed compounds are outweighed by the therapeutically beneficial effects.

In one embodiment, the therapeutic result can be reducing, inhibiting or preventing cancer metastasis or invasiveness of the cancer cells or metastasis, or reducing, alleviating, inhibiting or preventing at least one symptoms of the metastasis thereof, or any other desired alteration of a biological system. In another embodiment, the therapeutic result may be reducing, inhibiting, or preventing restenosis in a patient susceptible to restenosis.

An "effective treatment" refers to treatment producing a beneficial effect, e.g., amelioration of at least one symptom of the disease. A beneficial effect can take the form of an improvement over baseline, i.e., an improvement over a measurement or observation made prior to initiation of therapy according to the method. A beneficial effect can also take the form of reducing or inhibiting at least one symptom of the disease or reducing, alleviating, inhibiting or preventing at least one symptoms of the disease thereof.

The present invention also provides methods of inhibiting or reducing restenosis in a patient in need thereof, the method comprising administering the compound or the composition comprising the compound to the subject in an effective amount to reduce or inhibit restenosis in the patient.

Restenosis refers to the recurrence of stenosis, or the narrowing of a blood vessel which leads to restricted blood flow. Restenosis occurs mainly in an artery or other large blood vessel that has become narrowed and received treatment to clear the blockage and subsequently become renarrowed. In some embodiments, the subject has undergone an endovascular procedure, such as, for example but not limited to, vascular surgery, cardiac surgery, angioplasty or stent implantation.

For restenosis, the beneficial effect may be the reduction, inhibition or prevention of the re-narrowing of arteries or blood vessels within the subject, reduction or prevention of chest pain (angina), major or minor heart attack (myocardial infarction), stroke or other symptoms associated with narrowing of blood vessels. Suitable methods of measuring narrowing of blood vessels are known in the art, including imaging.

The PAR1 modulators of the present invention provide cytoprotection for endothelial cells, for example, in coronary blood vessels and tissues after a heart attack.

By "prevent" or "preventing" we mean preventive measures intended to inhibit undesirable physiological changes or the development of a metastasis or restenosis. In exemplary embodiments, preventing metastasis comprises initiating the administration of a prophylactically effective amount of a composition comprising the compounds described herein at a time prior to the appearance or existence of a metastasis such that metastases, or its symptoms, pathological features, consequences, or adverse effects do not occur. In such cases, a method of the invention for preventing metastasis comprises administering a composition comprising the compounds described herein to a subject in need thereof such as an a cancer patient susceptible to metastasis.

In further exemplary embodiments, preventing restenosis comprises initiating the administration of a prophylactically effective amount of a composition comprising the compounds described herein at a time prior to the appearance or existence of a restenosis, such as after stent implantation or angioplasty, such that restenosis, or its symptoms, pathological features, consequences, or adverse effects do not occur. In such cases, a method of the invention for preventing restenosis comprises administering a composition comprising the compounds described herein to a subject in need thereof such as a patient that has undergone angioplasty or stent implantation.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the compounds of the present invention, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the compounds of the present invention is administered to a subject or is used in an assay or other method described herein or a cited reference, e.g., within about 1 hour of the administration or use of the compounds of the present invention to about 3, 6, 9 months or more after a subject(s) has received the compounds of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self-assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the compounds of the present invention is administered to a subject or is used in an assay or other method described herein or a cited reference, e.g., within about 1 hour of the administration or use of the compounds of the present invention to about 3, 6, 9 months or more after a subject(s) has received the compounds of the present invention.

A "prophylactically effective amount" refers to an amount effective, at dosages and for periods of time necessary, to achieve the desired prophylactic result, such as preventing or inhibiting the disease. A prophylactically effective amount can be determined as described above for the therapeutically effective amount. Typically, since a prophylactic dose is used in subjects prior to or at an earlier stage of disease diagnosis or before symptoms, e.g., restenosis, kidney disease, proliferative disease, etc. can occur, the prophylactically effective amount will be less than the therapeutically effective amount.

By "administering" we mean any means for introducing the compounds of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

By "subject" or "patient" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. In a preferred embodiment, the subject is a human. The term "subject" does not denote a particular age or sex.

The present invention has been described in terms of one or more preferred embodiments, and it should be appreciated that many equivalents, alternatives, variations, and modifications, aside from those expressly stated, are possible and within the scope of the invention.

ABBREVIATIONS aPC, activated Protein C; Boc, tert-butoxycarbonyl; DCE, 1,2-dichloroethane; DCM, dichloromethane; DIC, disseminated intravascular coagulation; DIEA, N,N-diisopropylethylamine; DMAP, 4-dimethylaminopyridine; DMF, N,N-dimethylformamide; DMSO, dimethylsulfoxide; EDC, 1-ethyl-3-(3-dimethylaminopropyl)carbodiimide; FDA, U.S. Food and Drug Administration; GPCR, G-protein coupled receptor; HATU, hexafluorophosphate azabenzotriazole tetramethyl uronium; HOBt, 1-hydroxybenzotriazole; HTS, high-throughput screening; HUVEC, human umbilical vein endothelial cells; $IC_{50}$, half-maximal inhibitory concentration; $iCa^{2+}$, intracellular calcium mobilization; LC-MS, liquid chromatography-mass spectrometry; MI, myocardial infarction; NMR, nuclear magnetic resonance; PAR, Protease-activated receptor; qPCR, quantitative polymerase chain reaction; SAR, structure-activity relationship; SEM, standard error of the mean; TF, tissue factor; TNF-α, Tumor Necrosis Factor-alpha.

The invention will be more fully understood upon consideration of the following non-limiting examples.

EXAMPLES

Example 1: Parmodulin NRD-21 is an Allosteric Inhibitor of PAR1 Gq Signaling with Improved Anti-Inflammatory Activity and Stability The embodiments described in Example 1 demonstrate various materials, methods, and results related to and supportive of the present invention, but is in no way limiting to the scope of the claims.

Novel analogs of the allosteric, biased PAR1 ligand ML161 (parmodulin 2, PM2) were prepared in order to identify potential anti-thrombotic and anti-inflammatory compounds of the parmodulin class with improved properties. Investigations of structure-activity relationships of the western portion of the 1,3-diaminobenzene scaffold were performed using an intracellular calcium mobilization assay with endothelial cells, and several heterocycles were identified that inhibited PAR1 at sub-micromolar concentrations. The oxazole NRD-21 was profiled in additional detail, and it was confirmed to act as a selective negative allosteric modulator of PAR1 that inhibits human platelet aggregation. It showed superior anti-inflammatory activity to ML161 in a qPCR assay measuring the expression of tissue factor in response to the cytokine TNF-alpha in endothelial cells. Additionally, NRD-21 is much more plasma stable than ML161, and is a promising lead compound for the parmodulin class for anti-thrombotic and anti-inflammatory indications.

The use of biased ligands for G-protein coupled receptors (GPCRs) has emerged as a promising strategy for maximizing therapeutic signals mediated by GPCRs, while potentially mitigating undesired side effects linked to alternative signaling pathways initiated by the same receptors. Protease-activated receptors (PARs) are GPCRs that are activated by a variety of vascular proteases that cleave the N-termini of PARs, revealing a tethered peptide that activates the receptor[1] and initiates a plethora of signals.[2] PARs are present in a variety of tissues and are implicated in a variety of pathologies including thrombosis, inflammation, and cancer cell metastasis.[3,4] The varied phenotypic effects of PAR activation have recently been connected to the activation of specific G-proteins and arrestins,[5] and biased signals have been observed with proteases such as activated protein C (aPC) that cleave PAR N-termini at alternative sites.[6-10] Synthetic peptides[11,12] and peptidomimetics[13,14] based on PAR tethered ligands have also shown biased signaling by blocking or activating only a subset of signals, and pepducins, a novel class of fatty acid-tethered peptides modeled after intracellular GPCR loops developed by Kuliopulos and coworkers,[15-17] have been reported to act as biased antagonists at PAR2.[4,18] Previously, we reported that small molecules identified via high-throughput screening (HTS) are capable of inhibiting platelet granule secretion, while permitting the shape change of platelets normally observed upon platelet activation via PAR1 agonism, thus acting as "biased antagonists" of PAR1.[19,20] Our collaborators (Flaumenhaft and coworkers) have accrued evidence that these small molecules, termed parmodulins, act at the intracellular side of PAR1 to block signaling mediated by Gq, but not G12/13.[21,22] The parmodulin ML161 (1, also referred to as parmodulin 2 or PM2) was found to promote cytoprotective and anti-inflammatory effects in endothelium in a manner similar to aPC,[22] and as with aPC it was highly effective at minimizing necrosis of coronary tissue in a mouse model of myocardial infarction (MI).[23] We also recently confirmed that ML161 and its aniline analog RR-90 are selective, reversible, and allosteric inhibitors (negative allosteric modulators) of PAR1 signaling via the G-protein Gq.[24] The presence of PAR1 is required for the cytoprotective effects of aPC[25] and ML161[21,22] in endothelium, and targeting PAR1 with parmodulins to inhibit pro-inflammatory or pro-thrombotic signals while activating beneficial anti-inflammatory and/or cytoprotective signals could be an effective therapeutic strategy for sepsis, stroke, and thrombosis. This Example describes our efforts to more deeply explore structure-activity relationships (SARs) at the western side of parmodulins possessing the 1,3-diaminobenzene scaffold, exemplified by ML161.

ML161 was previously assigned as a Molecular Libraries probe,[20,26] and was our most potent analog to date in the P-selectin assay, a flow cytometry assay which measures levels of P-selectin on the surface of activated platelets. Our interest in measuring the effects of parmodulins in endothelial cells led us to develop a protocol for an intramolecular calcium mobilization ($iCa^{2+}$) assay using adherent Ea.hy926 cells in 96 well plates.[24] This assay also offers higher throughput and lower variability than the platelet P-selectin assay, so we have utilized it as our primary assay for our ongoing studies. Compounds were screened in 96 well plates at a concentration of 10 μM, using the PAR1 tethered ligand peptide TFLLRN (5 μM) as agonist. 7-point concentration-response curves were obtained for compounds demonstrating >70% inhibition in this screen.

A significant liability of ML161 is its low stability in mouse plasma. Therefore, we focused our efforts on finding alternative analogs that could offer equal or better potency than ML161 in the $iCa^{2+}$ assay but with improved plasma stability, which is particularly important for longer duration in vivo experiments.

EXPERIMENTAL SECTION a) Compound synthesis

All reagents and solvents, including anhydrous solvents, were purchased from commercial vendors and used as received. Deionized water was purified by charcoal filtration to a minimum resistance of 15 MΩ and used for reaction workups and in reactions with water. NMR spectra were recorded on Varian 300 MHz or 400 MHz spectrometers as indicated. Filtration was performed by vacuum using VWR Grade 413 filter paper, unless otherwise noted. Flash chromatography was performed using Biotage SNAP cartridges filled with 40-60 μm silica gel on Biotage Isolera automated chromatography systems with photodiode array UV detectors. Analytical thin layer chromatography (TLC) was performed on Agela Technologies 0.25 mm glass plates with 0.25 mm silica gel. Visualization was accomplished with UV light (254 nm) and $KMnO_4$ stain, unless otherwise noted. Chemical names were generated and select chemical properties were calculated using either ChemAxon Marvin suite or ChemDraw Professional 15.1. NMR data were processed using either MestreNova or ACD/NMR Processor Academic Edition using the JOC report format. High-resolution mass spectra (HRMS) were obtained from the University of Cincinnati Environmental Analysis Service Center using an Agilent 6540 Accurate-Mass LC-MS with Q-TOF.

LC-MS characterization methods

Tandem liquid chromatography/mass spectrometry (LC-MS) was performed on a Shimadzu LCMS-2020 with autosampler, photodiode array detector, and single-quadrupole MS with ESI and APCI dual ionization using a Peak Scientific nitrogen generator.

Method A Column: Phenomenex Gemini Cis (100×4.6 mm, 3 μm particle size, 110 Å pore size) Column temperature: 40° C. Sample Injection: 1-5 μL of sample in MeCN or MeOH Chromatographic monitoring: UV absorbance at 210 or 254 nm Mobile Phase: Solvent A: $H_2O$ w/0.1% formic acid; Solvent B: MeCN w/0.1% formic acid Flow Rate: 1.0 mL/min Gradient: 0 to 0.1 min: 25% MeCN 0.1 min to 5 min: 25% to 95% MeCN 5 min to 7 min: 95% MeCN 7 min to 9 min: 25% MeCN Method B Column: Phenomenex Gemini $C_{18}$(100×4.6 mm, 3 μm particle size, 110 Å pore size) Column temperature: 40° C. Sample Injection: 1-5 μL of sample in MeCN or MeOH Chromatographic monitoring: UV absorbance at 210 or 254 nm Mobile Phase: Solvent A: $H_2O$ w/0.1% formic acid; Solvent B: MeOH w/0.1% formic acid Flow Rate: 1.0 mL/min Gradient: 0 to 0.1 min: 25% MeOH 0.1 min to 5 min: 25% to 95% MeOH 5 min to 7 min: 95% MeOH 7 min to 9 min: 25% MeCN Method C Column: Phenomenex Gemini $C_{18}$ (100×4.6 mm, 3 μm particle size, 110 Å pore size) Column temperature: 40° C. Sample Injection: 1-5 μL of sample in MeCN or MeOH Chromatographic monitoring: UV absorbance at 210 or 254 nm Mobile Phase: Solvent A: $H_2O$ w/0.1% formic acid; Solvent B: MeCN w/0.1% formic acid Flow Rate: 1.0 mL/min Gradient: 0 to 0.1 min: 50% MeCN 0.1 min to 3 min: 50% to 95% MeCN 3 min to 5 min: 95% MeCN 5 min to 7 min: 50% MeCN General Amide Coupling Protocols Method A: Amide coupling using EDC To a round bottom flask with stir bar under nitrogen were added the appropriate carboxylic acid and anhydrous DCM/DMF (85:15; 0.2-0.6 M). The amine HCl salt to be coupled (1.2 eq.), HOBt (1.2 eq.), EDC-HCl (1.2 eq.), and DIPEA (2.1 eq.) were added and the reaction was stirred under nitrogen. The reaction was diluted with DCM (75 mL), washed with saturated $NaHCO_3$, 1M HCl (30 mL), brine, dried over $Na_2SO_4$, filtered, and concentrated under reduced pressure to give crude product.

Method B: Amide coupling using EDC without acid wash

To a round bottom flask with stir bar under nitrogen were added the appropriate amine salt and anhydrous DCM/DMF (85:15; 0.2-0.6 M). The carboxylic acid to be coupled (1.2 eq.), HOBt (1.2 eq.), EDC-HCl (2 eq.), and DIPEA (3 eq.) were added and the reaction was stirred under nitrogen. The reaction was diluted with water and DCM (75 mL), washed with saturated $NaHCO_3$, brine, dried over $Na_2SO_4$, filtered, and concentrated under reduced pressure to give crude product.

Method C: Conversion to the acid chloride for subsequent acylation

To an oven-dried round bottom flask with stir bar under nitrogen were added the carboxylic acid, dry DCM, and 3 Å molecular sieves. Oxalyl chloride (1.2 eq.) and a catalytic amount of DMF (1-2 mol %) were added and the reaction was stirred while attached to a bubbler (to monitor production of $CO_2$) at 20° C. for 2-3 h. The amine HCl salt (1 eq.) in DCM and DIPEA (2 eq.) were added and the reaction was stirred under nitrogen for 3-6 h. The reaction was diluted with EtOAc and washed with half-saturated aqueous $NaHCO_3$, 1M HCl (30 mL), brine, dried over $Na_2SO_4$, filtered, and concentrated under reduced pressure to give crude material.

Synthetic procedures for selected parmodulins

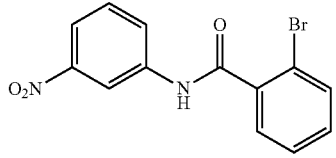

1

2-bromo-N-(3-nitrophenyl)benzamide (1)

1 was synthesized according to a previously published protocol (*ACS Med. Chem. Lett.* 2012, 3, 232-237)

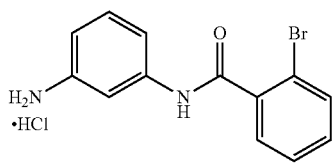

2

N-(3-aminophenyl)-2-bromobenzamide hydrochloride (2)

To a round bottom flask with stir bar was added a solution of $SnCl_2 \cdot 2H_2O$ (6.15 g, 0.03 mol) in conc. HCl (5 mL). To this solution was added a solution of 2-bromo-N-(3-nitrophenyl)benzamide (1, 1.75 g, 0.01 mol) in ethanol (50 mL), and the resulting suspension was stirred at 55° C. for 2 h. A sample aliquot was taken from the reaction, basified with 2M aq. NaOH, filtered, and the filtrate was concentrated under reduced pressure, dissolved in a minimal amount of HPLC grade MeCN, and analyzed by LC-MS to confirm reaction completion. The reaction was cooled to 20° C., basified with 2 M aq. NaOH (until pH 9), and filtered. The filtrate was concentrated under reduced pressure to half volume and then extracted with DCM (150 mL). The organic layer was washed with brine, dried over $Na_2SO_4$, filtered, and concentrated under reduced pressure to give crude product. The crude material was dissolved in DCM and added to 0.9 M HCl in ether (20 mL) and stirred for 5 min. at 20° C. to form a precipitate. The precipitate was filtered, washed with DCM, collected, and dried to give aniline HCl salt 2 (1.6 g, 81%) as a yellow solid. This compound has been previously reported and characterized (CAS# 331445-38-6).

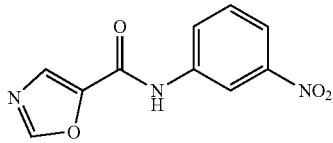

3

N-(3-nitrophenyl)-1,3-oxazole-5-carboxamide (3)

Oxazole-5-carboxylic acid was coupled to 3-nitroaniline using general amide coupling method A. The crude product was dissolved in a minimal amount of DCM, loaded onto a 100 g silica column, and purified by flash chromatography (EtOAc:hexanes, 0-100%) to give 3 as a yellow solid (1.50 mg) in 40% yield. LC/MS tR=5.94 min (Characterization Method A); m/z=231.90 (M−H).

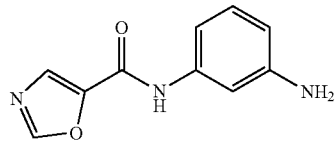

4

N-(3-aminophenyl)-1,3-oxazole-5-carboxamide (4)

To a high-pressure hydrogenator flask was added compound 3 (240 mg, 1.03 mmol) and a magnetic stir bar. The staring material was dissolved in methanol (40 mL) and then flushed with nitrogen gas for 5 minutes. Under nitrogen was added Pd/C (10%, 56.0 mg, 0.0526 mmol) and then the vessel was sealed shut. The reaction flask was evacuated and then gassed and degassed with hydrogen three times. The reaction was stirred at room temperature at 15 bar for 1 hour. The reaction mixture was then passed through a silica plug and concentrated to yield aniline 4 (187 mg, 895) as an off-white solid. LC/MS tR=1.46 min (Characterization Method A); m/z=203.65 (M+H).

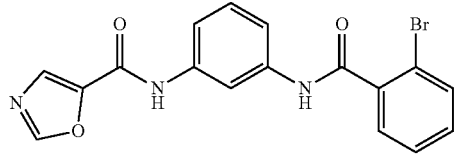

5

N-[3-(2-bromobenzamido)phenyl]-1,3-oxazole-5-carboxamide (5)

Oxazole-5-carboxylic acid was coupled to amine 2 using general amide coupling method A. The crude product was dissolved in a minimal amount of DCM, loaded onto a 10 g silica column, and purified by flash chromatography (MeOH:DCM, 0-8%) to give 5 as a clear yellow oil (40 mg, 60%). LC/MS tR=4.29 min (Characterization Method A); m/z=387.29 (M+H).

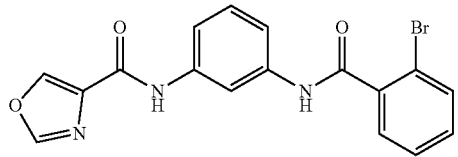

6

N-[3-(2-bromobenzamido)phenyl]-1,3-oxazole-4-carboxamide (6)

Oxazole-4-carboxylic acid was coupled to amine 2 using general amide coupling method A. The crude product was dissolved in a minimal amount of DCM, loaded onto a 10 g silica column, and purified by flash chromatography (MeOH:DCM, 0-8%) to give 6 as a yellow oil (19 mg, 29%). LC/MS tR=4.56 min (Characterization Method A); m/z=387.70 (M+H).

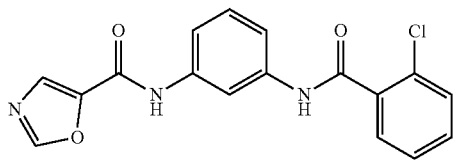

N-[3-(2-chlorobenzamido)phenyl]-1,3-oxazole-5-carboxamide (7)

2-Chlorobenzoic acid was coupled to amine 4 using general amide coupling method A. The crude product was dissolved in a minimal amount of DCM, loaded onto a 10 g silica column, and purified by flash chromatography (MeOH:DCM, 0-8%) to give 7 as an off-white solid (30 mg, 44%). LC/MS tR=4.50 min (Characterization Method A); m/z=341.95 (M+H).

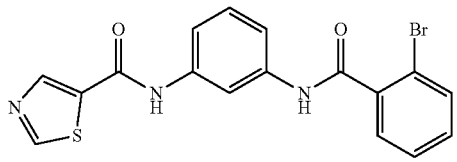

N-[3-(2-bromobenzamido)phenyl]-1,3-thiazole-5-carboxamide (8)

Thiazole-5-carboxylic acid was coupled to amine 2 using general amide coupling method A. The crude product was dissolved in a minimal amount of DCM, loaded onto a 10 g silica column, and purified by flash chromatography (EtOAc:hexanes, 0-80%) to give 8 as an off-white solid (39 mg, 56%). LC/MS tR=5.23 min (Characterization Method A); m/z=403.70 (M+H).

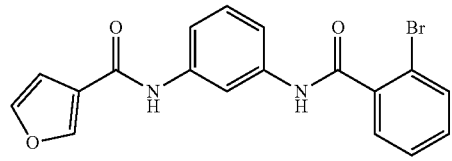

N-[3-(2-bromobenzamido)phenyl]furan-3-carboxamide (9)

Furan-3-carboxylic acid was coupled to amine 2 using general amide coupling method A. The crude product was dissolved in a minimal amount of DCM, loaded onto a 10 g silica column, and purified by flash chromatography (EtOAc:hexanes, 0-80%) to give 9 as a yellow oil (9 mg, 14%). LC/MS tR=4.84 min (Characterization Method A); m/z=384.85 (M+H).

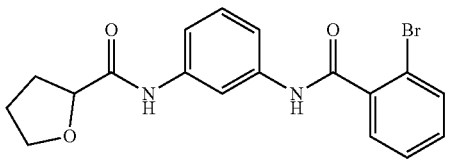

N-[3-(2-bromobenzamido)phenyl]oxolane-2-carboxamide (10)

Tetrahydrofuran-2-carboxylic acid was coupled to amine 2 using general amide coupling method C. The crude product was dissolved in a minimal amount of DCM, loaded onto a 10 g silica column, and purified by flash chromatography (EtOAc:hexanes, 0-100%) to give 10 as an off-white solid (45 mg, 66%). LC/MS tR=3.47 min (Characterization Method C); m/z=390.05 (M+H).

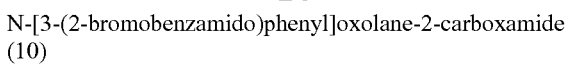

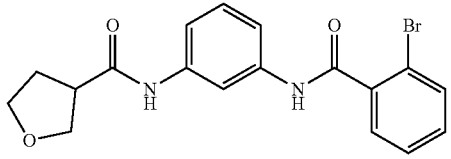

N-[3-(2-bromobenzamido)phenyl]oxolane-3-carboxamide (11)

Tetrahydrofuran-3-carboxylic acid was coupled to amine 2 using general amide coupling method C. The crude product was dissolved in a minimal amount of DCM, loaded onto a 10 g silica column, and purified by flash chromatography (EtOAc:hexanes, 0-100%) to give 11 as an off-white solid (29 mg, 44%). LC/MS tR=2.46 min (Characterization Method C); m/z=390.05 (M+H).

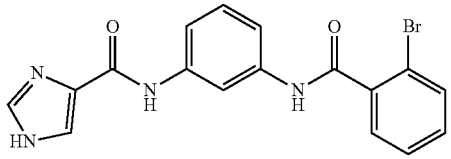

N-[3-(2-bromobenzamido)phenyl]-1H-imidazole-4-carboxamide (12)

1H-imidazole-4-carboxylic acid was coupled to amine 2 using general amide coupling method B. The desired product was obtained by triturating the crude product with ice cold DCM, yielding 12 as a white solid (11 mg, 17%). LC/MS tR=4.34 min (Characterization Method A); m/z=384.75 (M+H).

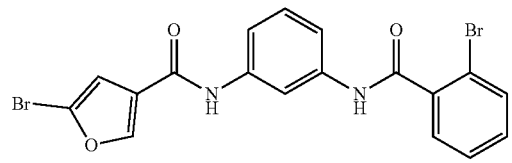

5-bromo-N-[3-(2-bromobenzamido)phenyl]furan-3-carboxamide (13)

4-Bromofuran-3-carboxylic acid was coupled to amine 2 using general amide coupling method A. The crude product was dry loaded onto Celite and purified by flash chromatography (MeOH:DCM as 0.1 M TEA solutions) using a 10 g silica column, to give 13 as a white solid (16 mg, 31%). LC/MS tR=6.99 min (Characterization Method B); m/z=420.70 (M+H).

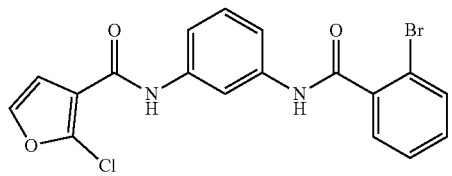

N-[3-(2-bromobenzamido)phenyl]-2-chlorofuran-3-carboxamide (14)

2-Chlorofuran-3-carboxylic acid was coupled to amine 2 using general amide coupling method A. The crude product was dissolved in a minimal amount of DCM, loaded onto a 5 g silica column, and purified by flash chromatography (MeOH:DCM, 0-5%) to give 14 as a brown solid (28 mg, 27%). LC/MS tR=6.13 min (Characterization Method B); m/z=420.70 (M+H).

Assay Results

The intracellular calcium mobilization assay was performed with Ea.hy926 cells according to our published protocol (*Bioorg. Med. Chem.* 2018, 9, 2514-2529), using TFLLRN-NH$_2$ as PAR1 agonist.

| Cmpd | R$_1$ | R$_2$ | iCa$^{2+}$ assay$^a$ % Inhib; pIC$_{50}$ |
|---|---|---|---|
| 5 NRD-21 | oxazol-5-yl | 2-Br-phenyl | 59 ± 13% 6.3 ± 0.1 |
| 6 | oxazol-4-yl | 2-Br-phenyl | 82 ± 1% 6.4 ± 0.1 |
| 7 | oxazol-4-yl | 2-Cl-phenyl | 66 ± 13%; 6.4 ± 0.2 |
| 8 | thiazol-5-yl | 2-Br-phenyl | 56 ± 6%; 7.03 ± 0.03 |
| 9 | furan-3-yl | 2-Br-phenyl | 97 ± 13%; 7.39 ± 0.12 |
| 10 | tetrahydrofuran-2-yl | 2-Br-phenyl | 42 ± 3% |
| 11 | tetrahydrofuran-3-yl | 2-Br-phenyl | 44 ± 2% |
| 12 | 1H-imidazol-4-yl | 2-Br-phenyl | — |
| 13 | 5-bromofuran-3-yl | 2-Br-phenyl | — |
| 14 | 2-chlorofuran-3-yl | 2-Br-phenyl | — |

$^a$Assays were performed with adherent EA.hy926 endothelial cells. % Inhibition was measured at 10 μM with 5 μM TFLLRN-NH$_2$ and n=4 wells, unless otherwise noted, with standard error of the mean (SEM) provided. pIC$_{50}$s (-logIC$_{50s}$) were estimated from curves fitted to measurements on 3 separate wells for each concentration, using 4-variable non-linear regression in GraphPad Prism v.6.

Figure 5A:
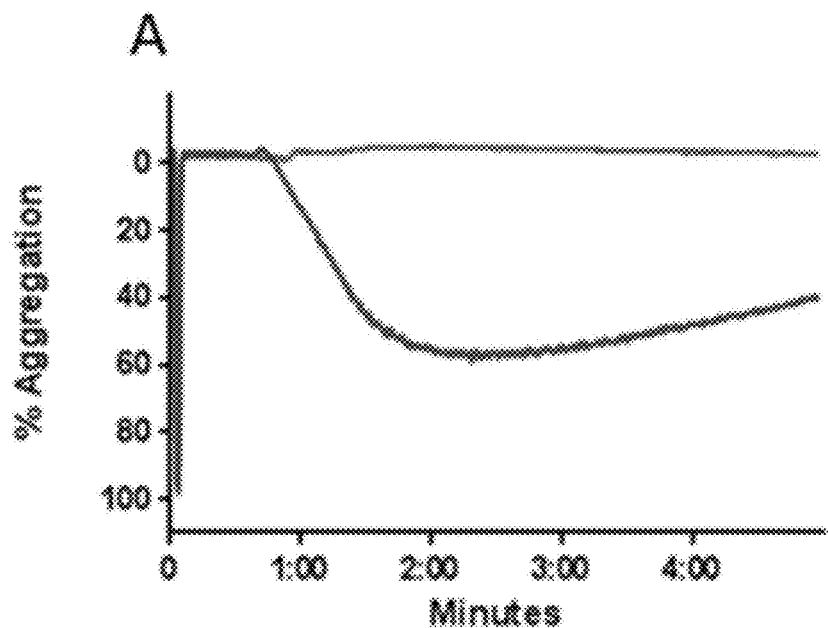
FIGS. 5A-5B depicts results of a human platelet aggregation assay of A) ML161 (10 µM, red trace) and B) NRD-21 (10 µM, red trace) in the presence of the PAR1/2 agonist SFLLRN-NH$_2$ (2 µM). Blue traces=DMSO.
Figure 5B:
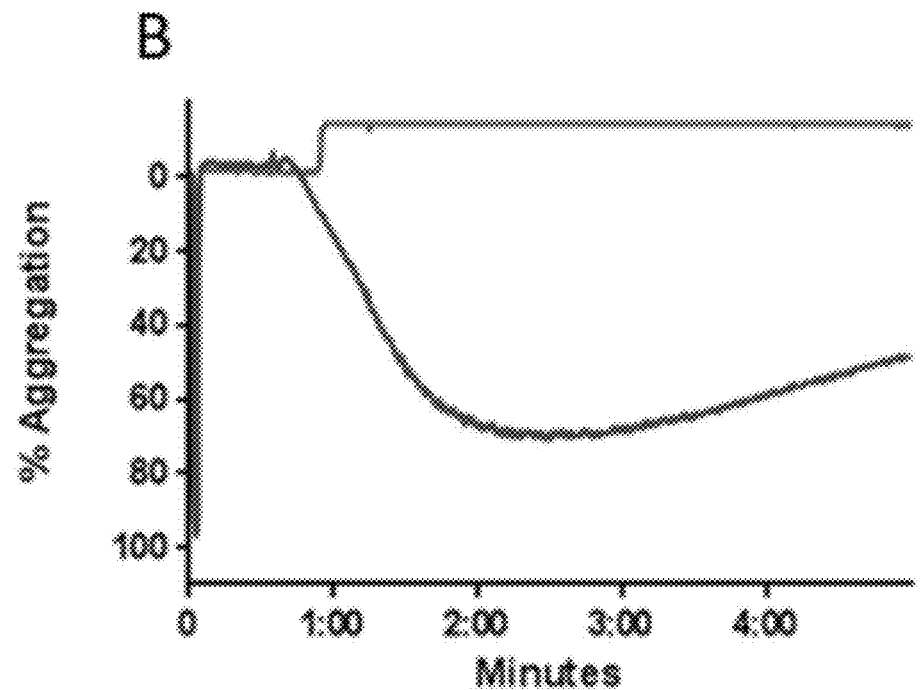

Next, an assay was performed to measure the ability of NRD-21 to inhibit platelet aggregation. PAR1 is highly expressed in platelets, and its activation leads to aggregation and coagulation. The platelet aggregation assay was performed with ML161 and NRD-21. In both cases, human washed platelets were incubated with parmodulins at 10 μM, then the PAR1/2 agonist SFLLRN-NH$_2$ (5 μM) was added. (FIG. 5). Complete inhibition of platelet aggregation by both ML161 and NRD-21 was observed.

Figure 6:
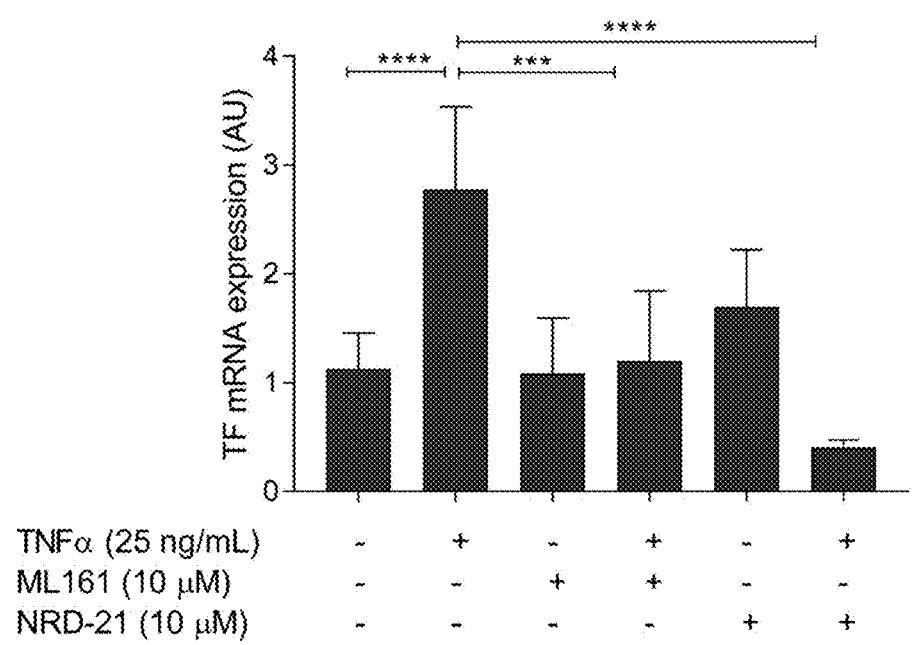
FIG. 6 is a graph depicting results of a qPCR assay (n=3) measuring the inhibition of TNF-α (25 ng/mL) induced tissue factor (TF) expression in HUVEC after treatment with ML161 and NRD-21 (10 µM). Inhibitors were added at t=0, TNF-α was added at t=1 h, and mRNA was measured at t=4 h.

NRD-21 showed anti-inflammatory properties as shown in FIG. 6. To this end, we performed a qPCR assay measuring the expression of tissue factor (TF) in endothelial cells (HUVEC) in response to the inflammatory cytokine Tumor Necrosis Factor-alpha (TNF-α). TF has been long established to mediate the pro-inflammatory and pro-coagulant effects[27] of TNF-α[28,29] and endotoxins,[30] and unnatural TF expression is therefore the driver of disseminated intravascular coagulation (DIC) observed under conditions of cancer or sepsis.[31] We measured the level of TF mRNA 4 h after treatment with ML161 or NRD-21 followed by the addition of TNF-α (FIG. 6). Pretreatment with ML161 (column 4) blocked the ~3-fold increase in TF expression caused by TNF-α alone (column 1), and NRD-21 was even more efficacious, dropping TF RNA levels to below baseline levels.

We measured its stability and a number of parameters relevant to its use as an in vivo probe (Table 5, FIG. 7). Importantly, NRD-21 is much more plasma stable than ML161. After 4 h in mouse plasma, 32% of NRD-21 remained, while ML161 was less than 1%.

Figure 8:
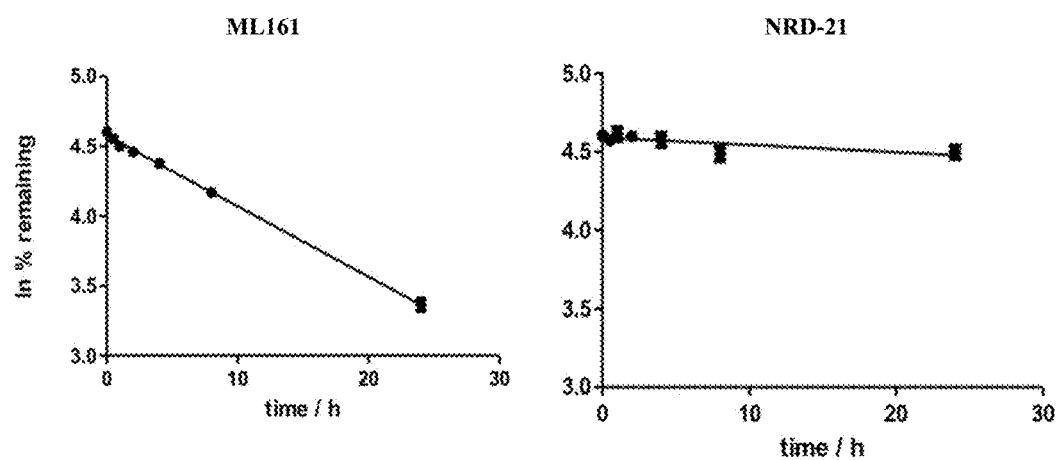
FIG. 8. Human plasma stability of ML161 (left) and NRD-21 (right). Points indicate the natural logarithm of the average concentration of compound remaining, with 3 replicates at each time point.

Improved stability in human plasma was also observed for NRD-21 (97% vs 79% after 4 h), as shown in FIG. 8. As with ML161, NRD-21 also shows excellent stability in the presence of human liver microsomes, with no apparent degradation after 1 h. It also shows no measurable toxicity in a human cell line (hepG2). An area for improvement remains the low solubility of the current lead compounds of this class, with a solubility of 17 µM for NRD-21 in a kinetic aqueous solubility assay with 2.5% DMSO. Both compounds were also profiled for off-target receptor binding by the Psychoactive Drug Screening Program (PDSP).[32] Both modified radioligand binding to 3 or 4 different targets, including inhibition of binding to the peripheral benzodiazepine receptor (PBR) and activation of the serotonin transporter (SERT).

REFERENCES (1) Chen, J.; Ishii, M.; Wang, L.; Ishii, K.; Coughlin, S. R. Thrombin Receptor Activation. Confirmation of the Intramolecular Tethered Liganding Hypothesis and Discovery of an Alternative Intermolecular Liganding Mode. *J. Biol. Chem.* 1994, 269 (23), 16041-16045.

(2) Adams, M. N.; Ramachandran, R.; Yau, M.-K.; Suen, J. Y.; Fairlie, D. P.; Hollenberg, M. D.; Hooper, J. D. Structure, Function and Pathophysiology of Protease Activated Receptors. *Pharmacol. Ther.* 2011, 130 (3), 248-282.

(3) Ramachandran, R.; Noorbakhsh, F.; DeFea, K.; Hollenberg, M. D. Targeting Proteinase-Activated Receptors: Therapeutic Potential and Challenges. *Nat Rev Drug Discov* 2012, 11 (1), 69-86.

(4) Hollenberg, M. D.; Mihara, K.; Polley, D.; Suen, J. Y.; Han, A.; Fairlie, D. P.; Ramachandran, R. Biased Signalling and Proteinase-Activated Receptors (PARs): Targeting Inflammatory Disease. *British Journal of Pharmacology* 2014,171 (5), 1180-1194.

(5) Soh, U. J.; Trejo, J. Activated Protein C Promotes Protease-Activated Receptor-1 Cytoprotective Signaling Through B-Arrestin and Dishevelled-2 Scaffolds. *Proc. Natl. Acad. Sci. U.S.A.* 2011, 108 (50), E1372-E1380.

(6) Madhusudhan, T.; Wang, H.; Straub, B. K.; Grone, E.; Zhou, Q.; Shahzad, K.; Muller-Krebs, S.; Schwenger, V.; Gerlitz, B.; Grinnell, B. W.; Griffin, J. H.; Reiser, J.; Grone, H. J.; Esmon, C. T.; Nawroth, P. P.; Isermann, B. Cytoprotective Signaling by Activated Protein C Requires Protease-Activated Receptor-3 in Podocytes. *Blood* 2012, 119 (3), 874-883.

(7) Schuepbach, R. A.; Madon, J.; Ender, M.; Galli, P.; Riewald, M. Protease-Activated Receptor-1 Cleaved at R46 Mediates Cytoprotective Effects. *J. Thromb. Haemost.* 2012, 10 (8), 1675-1684.

(8) Mosnier, L. O.; Sinha, R. K.; Burnier, L.; Bouwens, E. A.; Griffin, J. H. Biased Agonism of Protease-Activated Receptor 1 by Activated Protein C Caused by Noncanonical Cleavage at Arg46. *Blood* 2012, 120 (26), 5237-5246.

(9) Bouwens, E.; Stavenuiter, F.; Mosnier, L. O. Mechanisms of Anticoagulant and Cytoprotective Actions of the Protein C Pathway. *Journal of Thrombosis and Haemostasis* 2013, 11 (s1), 242-253.

(10) Burnier, L.; Mosnier, L. O. Novel Mechanisms for Activated Protein C Cytoprotective Activities Involving Noncanonical Activation of Protease-Activated Receptor 3. *Blood* 2013, 122 (5), 807-816.

(11) Rasmussen, U. B.; Gachet, C.; Schlesinger, Y.; Hanau, D.; Ohlmann, P.; Van Obberghen-Schilling, E.; Pouysségur, J.; Cazenave, J. P.; Pavirani, A. A Peptide Ligand of the Human Thrombin Receptor Antagonizes Alpha-Thrombin and Partially Activates Platelets. *J. Biol. Chem.* 1993, 268 (19), 14322-14328.

(12) Ramachandran, R.; Mihara, K.; Mathur, M.; Rochdi, M. D.; Bouvier, M.; DeFea, K.; Hollenberg, M. D. Agonist-Biased Signaling via Proteinase Activated Receptor-2: Differential Activation of Calcium and Mitogen-Activated Protein Kinase Pathways. *Molecular Pharmacology* 2009, 76 (4), 791-801.

(13) Barry, G. D.; Suen, J. Y.; Le, G. T.; Cotterell, A.; Reid, R. C.; Fairlie, D. P. Novel Agonists and Antagonists for Human Protease Activated Receptor 2. *J. Med. Chem.* 2010, 53 (20), 7428-7440.

(14) Suen, J. Y.; Barry, G. D.; Lohman, R. J.; Halili, M. A.; Cotterell, A. J.; Le, G. T.; Fairlie, D. P. Modulating Human Proteinase Activated Receptor 2 with a Novel Antagonist (GB88) and Agonist (GB110). *British Journal of Pharmacology* 2012, 165 (5), 1413-1423.

(15) Covic, L.; Gresser, A. L.; Talavera, J.; Swift, S.; Kuliopulos, A. Activation and Inhibition of G Protein-Coupled Receptors by Cell-Penetrating Membrane-Tethered Peptides. *Proc. Natl. Acad. Sci. U.S.A.* 2002, 99 (2), 643-648.

(16) Carlson, K. E.; McMurry, T. J.; Hunt, S. W., III. Pepducins: Lipopeptide Allosteric Modulators of GPCR Signaling. *Drug Discovery Today: Technologies* 2012, 9 (1), e33-e39.

(17) Zhang, P.; Leger, A. J.; Baleja, J. D.; Rana, R.; Corlin, T.; Nguyen, N.; Koukos, G.; Bohm, A.; Covic, L.; Kuliopulos, A. Allosteric Activation of a G Protein-Coupled Receptor with Cell-Penetrating Receptor Mimetics. *Journal of Biological Chemistry* 2015, 290 (25), 15785-15798.

(18) Sevigny, L. M.; Zhang, P.; Bohm, A.; Lazarides, K.; Perides, G.; Covic, L.; Kuliopulos, A. Interdicting Protease-Activated Receptor-2-Driven Inflammation with Cell-Penetrating Pepducins. *Proceedings of the National Academy of Sciences* 2011, 108 (20), 8491-8496.

(19) Dowal, L.; Sim, D. S.; Dilks, J. R.; Blair, P.; Beaudry, S.; Denker, B. M.; Koukos, G.; Kuliopulos, A.; Flaumenhaft, R. Identification of an Antithrombotic Allosteric Modulator That Acts Through Helix 8 of PAR1. *Proceedings of the National Academy of Sciences* 2011, 108 (7), 2951-2956.

(20) Dockendorff, C.; Aisiku, O.; Verplank, L.; Dilks, J. R.; Smith, D. A.; Gunnink, S. F.; Dowal, L.; Negri, J.; Palmer, M.; Macpherson, L.; Schreiber, S. L.; Flaumenhaft, R. Discovery of 1,3-Diaminobenzenes as Selective Inhibitors of Platelet Activation at the PAR1 Receptor. *ACS Med Chem Lett* 2012, 3 (3), 232-237.

(21) Aisiku, O.; Peters, C. G.; De Ceunynck, K.; Ghosh, C. C.; Dilks, J. R.; Fustolo-Gunnink, S. F.; Huang, M.; Dockendorff, C.; Parikh, S. M.; Flaumenhaft, R. Parmodulins Inhibit Thrombus Formation Without Inducing Endothelial Injury Caused by Vorapaxar. *Blood* 2015, 125 (12), 1976-1985.

(22) De Ceunynck, K.; Peters, C. G.; Jain, A.; Higgins, S. J.; Aisiku, O.; Fitch-Tewfik, J. L.; Chaudhry, S. A.; Dockendorff, C.; Parikh, S. M.; Ingber, D. E.; Flaumenhaft, R. PAR1 Agonists Stimulate APC-Like Endothelial Cytoprotection and Confer Resistance to Thromboinflammatory Injury. *Proceedings of the National Academy of Sciences* 2018, 115 (5), E982-E991.

(23) Nazir, S.; Gadi, I.; Al-Dabet, M. M.; Elwakiel, A.; Kohli, S.; Ghosh, S.; Manoharan, J.; Ranjan, S.; Bock, F.; Braun-Dullaeus, R. C.; Esmon, C. T.; Huber, T. B.; Camerer, E.; Dockendorff, C.; Griffin, J. H.; Isermann, B.; Shahzad, K. Cytoprotective Activated Protein C Averts Nlrp3 Inflammasome-Induced Ischemia-Reperfusion Injury via mTORC1 Inhibition. *Blood* 2017, 130 (24), 2664-2677.

(24) Gandhi, D. M.; Majewski, M. W.; Rosas, R.; Kentala, K.; Foster, T. J.; Greve, E.; Dockendorff, C. Characterization of Protease-Activated Receptor (PAR) Ligands: Parmodulins Are Reversible Allosteric Inhibitors of PAR1-Driven Calcium Mobilization in Endothelial Cells. *Bioorganic & Medicinal Chemistry* 2018, 26 (9), 2514-2529.

(25) Mosnier, L. O.; Griffin, J. H. Inhibition of Staurosporine-Induced Apoptosis of Endothelial Cells by Activated Protein C Requires Protease-Activated Receptor-1 and Endothelial Cell Protein C Receptor. *Biochem. J.* 2003, 373 (Pt 1), 65-70.

(26) Verplank, L.; Dockendorff, C.; Negri, J.; Perez, J. R.; Dilks, J.; Macpherson, L.; Palmer, M.; Flaumenhaft, R.; Schreiber, S. L. *Chemical Genetic Analysis of Platelet Granule Secretion-Probe* 3; National Center for Biotechnology Information (US): Bethesda (Md.), 2010.

(27) Chu, A. J. Tissue Factor Mediates Inflammation. *Arch. Biochem. Biophys.* 2005, 440 (2), 123-132.

(28) Bevilacqua, M. P.; Pober, J. S.; Majeau, G. R.; Fiers, W.; Cotran, R. S.; Gimbrone, M. A. Recombinant Tumor Necrosis Factor Induces Procoagulant Activity in Cultured Human Vascular Endothelium: Characterization and Comparison with the Actions of Interleukin 1. *Proc. Natl. Acad. Sci. U.S.A.* 1986, 83 (12), 4533-4537.

(29) Nawroth, P. P.; Stern, D. M. Modulation of Endothelial Cell Hemostatic Properties by Tumor Necrosis Factor. *J. Exp. Med.* 1986, 163 (3), 740-745.

(30) Colucci, M.; Balconi, G.; Lorenzet, R.; Pietra, A.; Locati, D.; Donati, M. B.; Semeraro, N. Cultured Human Endothelial Cells Generate Tissue Factor in Response to Endotoxin. *Journal of Clinical Investigation* 1983, 71 (6), 1893-1896.

(31) Gando, S.; Levi, M.; Toh, C.-H. Disseminated Intravascular Coagulation. *Nat Rev Dis Primers* 2016, 2, 16037.

As can be appreciated, the results described in the above examples support the utility of the materials and methods described and claimed herein. Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific materials, methods, formulations, reaction/assay conditions, etc., herein illustrated and described, but embraces such modified forms thereof as come within the scope of the following claims.

The invention claimed is:

1. A compound of formula I:

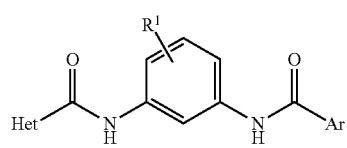

wherein
Het is selected from the group consisting of

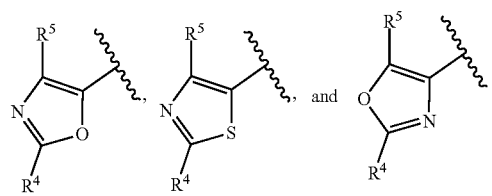

wherein
$R^1$ is H, Me, F, or Cl,
$R^4$ and $R^5$ are each independently selected from H, Me, F, Cl, and Br, and
Ar is a substituted benzene with at least one substitution selected from the group consisting of Br, F, Cl, —OH, fluoroalkyl and fluoroalkoxy.

2. The compound of claim 1, wherein both $R^4$ and $R^5$ are H.

3. The compound of claim 1, wherein either $R^4$ or $R^5$ is F, Cl or Br, and the other is H.

4. The compound of claim 1, wherein Het is selected from the group consisting of:

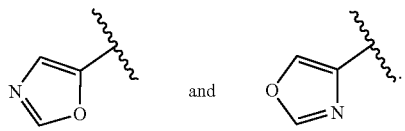 [SMILES: *c1cnco1 ; *c1cocn1]

5. The compound of claim 1, wherein the Ar is a benzene substituted with one halogen selected from Br, Cl, and F.

6. The compound of claim 1, wherein the Ar is 2-bromobenzene.

7. The compounds of claim 1, wherein Ar is a 2-chlorobenzene.

8. The compound of claim 1, wherein the Ar is a benzene substituted with Br and at least one additional substitution selected from the group consisting of F, Cl and OH.

9. The compound of claim 1, wherein the compound is selected from the group consisting of:

NRD-21

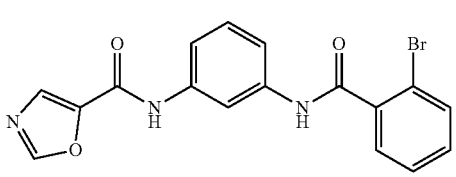

-continued

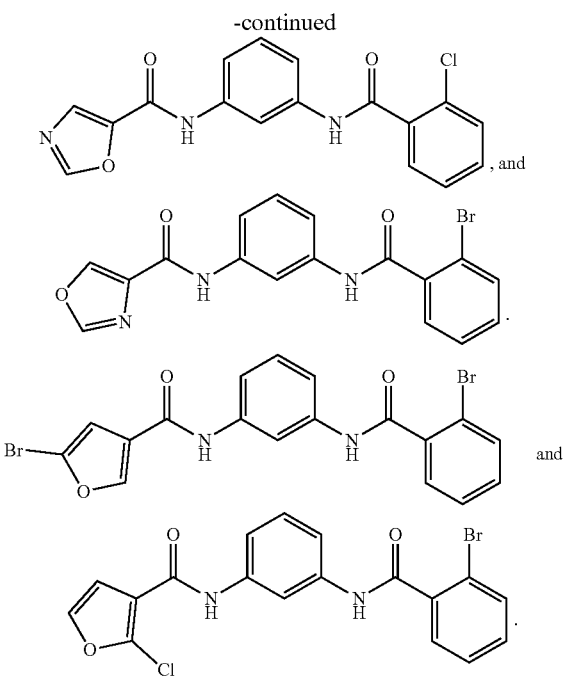

, and and

.

10. A composition comprising the compound of claim 1 and a pharmaceutically acceptable carrier.

11. A method of reducing, inhibiting or preventing thrombosis in a subject having or suspected of having a cardiovascular disease, the method comprising administering an effective amount of the compound of claim 1 to reduce, inhibit or prevent thrombosis.

12. The method of claim 11, wherein the cardiovascular disease is vascular injury, myocardial infarction, an ischemic disease, or stroke.

13. A method of therapeutically treating an inflammatory condition in a subject in need thereof, the method comprising administering an effective amount of the compound of claim 1 to therapeutically treat the inflammatory condition.

14. The method of claim 13, wherein the inflammatory condition is sepsis, the method comprising administering an effective amount of the compound of claim 1 to therapeutically treat the sepsis.

15. A method of therapeutically treating kidney disease in a subject having kidney disease, the method comprising administering an effective amount of the compound of claim 1 to therapeutically treat the kidney disease.

16. A method of therapeutically treating fibrosis in a subject having fibrosis, the method comprising administering an effective amount the compound of claim 1 to therapeutically treat the fibrosis.

* * * * *